(12) United States Patent
Lee et al.

(10) Patent No.: US 11,268,092 B2
(45) Date of Patent: Mar. 8, 2022

(54) STRUCTURE-ENGINEERED GUIDE RNA

(71) Applicant: GenEdit Inc., Berkeley, CA (US)

(72) Inventors: Kunwoo Lee, Berkeley, CA (US); Hunghao Chu, Berkeley, CA (US)

(73) Assignee: GenEdit, Inc., South San Francisco, CA (US)

( * ) Notice: Subject to any disclaimer, the term of this patent is extended or adjusted under 35 U.S.C. 154(b) by 502 days.

(21) Appl. No.: 16/247,311

(22) Filed: Jan. 14, 2019

(65) Prior Publication Data
US 2019/0218547 A1 Jul. 18, 2019

Related U.S. Application Data

(60) Provisional application No. 62/617,135, filed on Jan. 12, 2018.

(51) Int. Cl.
| *C12N 15/11* | (2006.01) |
| *C12N 9/22* | (2006.01) |
| *C12N 15/90* | (2006.01) |
| *C12N 15/113* | (2010.01) |

(52) U.S. Cl.
CPC ............ *C12N 15/11* (2013.01); *C12N 9/22* (2013.01); *C12N 15/907* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 2014/0349400 A1 | 11/2014 | Jakimo et al. |
| 2016/0289675 A1 | 10/2016 | Ryan et al. |

FOREIGN PATENT DOCUMENTS

| CN | 106 244 591 A | 12/2016 |
| WO | 2013/176772 A1 | 11/2013 |
| WO | 2015/013583 A2 | 1/2015 |
| WO | 2015/035139 A2 | 3/2015 |
| WO | 2016/022866 A1 | 2/2016 |
| WO | 2016/028843 A2 | 2/2016 |
| WO | 2016/065364 A1 | 4/2016 |
| WO | 2016/094867 A1 | 6/2016 |
| WO | 2016/182959 A1 | 11/2016 |
| WO | 2016/183402 A2 | 11/2016 |
| WO | 2017/040511 A1 | 3/2017 |
| WO | 2017/053312 A1 | 3/2017 |
| WO | 2017/064546 A1 | 4/2017 |
| WO | 2017/070598 A1 | 4/2017 |
| WO | 2017/180711 A1 | 10/2017 |
| WO | 2017/186550 A1 | 11/2017 |
| WO | 2017/207589 A1 | 12/2017 |
| WO | 2018/094356 A2 | 5/2018 |
| WO | 2019/070762 A1 | 4/2019 |

OTHER PUBLICATIONS

Zuris Ja, et al., "Cationic lipid-mediated delivery of proteins enables efficient protein-based genome editing in vitro and in vivo," *Nat. Biotech*, 33(1): pp. 73-80 (2015).
Schaffer DV et al., "Vector unpacking as a potential barrier for receptor-mediated polyplex gene delivery," *Biotechnol Bioeng*, 67(5): pp. 598-606 (2000).
Ousterout DG, et al., "Multiplex CRISPR/Cas9-based genome editing for correction of dystrophin mutations that cause Duchenne Muscular Dystrophy," *Nat. Commun*, 6:6244 (2015).
Durand G., et al., "A combinatorial approach to the repertoire of RNA kissing motifs; towards multiplex detection by switching hairpin aptamers," *Nucleic Acids Res.*, vol. 44(9): pp. 4450-4459 (2016).
Shu D., et al., "Thermodynamically stable RNA three-way junctions as platform for constructing multi-functional nanoparticles for delivery of therapeutics,"*Nat. Nanotechnol.*, vol. 6(10): pp. 658-667 (2011).
Yu J., et al., "De novo design of an RNA tile that self-assembles into a homo-octameric nanoprism," *Nat. Commun.* vol. 6:5724 (2014).
Sobczak, et al., "Structural Diversity of Triplet Repeat RNAs," *J. Biol. Chem.*, vol. 285(17): pp. 12755-12764 (2010).
Nowak, C. M. et al., "Guide RNA engineering for versatile Cas9 functionality," *Nucleic Acids Research*, vol. 44, No. 20, pp. 9555-9564 (2016).
Kelley, M. L. et al., "Versatility of chemically synthesized guide RNAs for CRISPR-Cas9 genome editing," *Journal of Biotechnology*, vol. 233, pp. 74-83 (2016).
Lee, K. et al., "Synthetically modified guide RNA and donor DNA are a versa title platform for CRISPR-Cas9 engineering," *eLife*, vol. 6 Article No. e25312, pp. 1-17 (2017).
Jinek et al., "RNA-programmed genome editing in human cells", *eLIFE, eLIFE Sciences Publications Ltd.*, vol. 2 (2013).
Yu et al., "Small Molecules Enhance CRISPR Genome Editing in Pluripotent Stem Cells", *Cell Stem Cell*, vol. 16, No. 2, pp. 142-147 (2015).
Pinder et al., "Nuclear domain 'knock-in' screen for the evaluation and identification of small molecule enhancers of CRISPR-based genome editing", *Nucleic Acids Research*, vol. 43, No. 19, pp. 9379-9392 (2015).
European Search Report in Application No. 17870720.4 dated Jun. 30, 2020.
Xu et al., "Generation of targeted mutant rice using a CRISPR-Cpf1 system", *Plant Biotechnology Journal*, vol. 15, No. 6, pp. 713-717 (Jun. 1, 2017).
Li, et al., "Engineering CRISPR-Cpf1 crRNAs and mRNAs to maximize genome editing efficiency", *Nature biomedical engineering*, vol. 1, No. 5, pp. 1-21 (May 10, 2017).
Dang et al., "Optimizing sgRNA structure to improve CRISPER-Cas9 knockout efficiency", *Genome Biology*, vol. 16, No. 280, pp. 1-10 (Jan. 1, 2015).
Zetsche et al., "Cpf1 Is a Single RNA-Guided Endonuclease of a Class 2 CRISPR-Cas System", *Cell*, vol. 163, No. 3, pp. 759-771 (Oct. 1, 2015).

*Primary Examiner* — Suzanne M Noakes
*Assistant Examiner* — Jae W Lee
(74) *Attorney, Agent, or Firm* — Leydig, Voit & Mayer, Ltd.

(57) ABSTRACT

The invention provides a modified guide RNA comprising an extension sequence, as well as related compositions and methods.

22 Claims, 9 Drawing Sheets

Specification includes a Sequence Listing.

STRUCTURE-ENGINEERED GUIDE RNA

CROSS-REFERENCE TO RELATED APPLICATIONS

This patent application claims priority to U.S. provisional patent application 62/617,135 filed on Jan. 12, 2018, the entire disclosure of which is hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 24,967 Byte ASCII (Text) file named "512725_ST25.TXT", created on Oct. 20, 2021.

BACKGROUND OF THE INVENTION

Genome editing based on CRISPR/Cas (clustered regularly interspaced short palindromic repeat/CRISPR-associated protein) technology greatly simplifies the process of gene editing, and has revolutionized biomedical research. Many human disorders caused by genetic mutations are potentially curable by this technology.

While studies have demonstrated efficacy of CRISPR/Cas system in correcting genetic mutations, widespread clinical translation of this technology requires safe and effective strategies to deliver the components of the CRISPR/Cas system (e.g., guide RNA, an RNA-guided endonuclease, and, in some cases, a donor nucleic acid) into a cell containing the genetic material to be edited. Viral methods exist, but toxicity and immunogenicity from the viral components pose safety concerns. Non-viral methods often lack efficiency.

Thus, there remains a need for compositions and methods for delivering CRISPR/Cas system components to cells to enable gene editing.

BRIEF SUMMARY OF THE INVENTION

Provided herein are structure-engineered guide RNA molecules useful in CRISPR/Cas gene editing systems. In one aspect, the invention provides a guide RNA (gRNA) comprising an extension sequence (e.g., on the 3' end of the gRNA), wherein the extension sequence comprises about 8 nucleotides or more. In another aspect, a tracrRNA is provided, which comprises an extension sequence on the 3' end, 5' end, or both of the tracrRNA, wherein the extension sequence comprises about 8 nucleotides or more. In yet another aspect, the invention provides a crRNA comprising an extension sequence on the 3' end of the crRNA, wherein the extension sequence comprises about 8 nucleotides or more.

Also provided is a composition comprising the modified gRNA, tracrRNA, or crRNA and a vehicle, optionally together with one or more additional components of the CRISPR/Cas system.

Still further provided is a method of editing a gene in a cell, the method comprising contacting the cell with the modified gRNA, tracrRNA, or crRNA or composition comprising same, optionally with a donor nucleic acid, wherein the cell comprises an RNA-guided endonuclease or an RNA-guided endonuclease is introduced into the cell, and whereupon the modified sgRNA enters the cell and a target gene in the cell is edited.

These and other aspects of the invention are described in greater detail in the following sections.

DETAILED DESCRIPTION OF THE INVENTION

Figure 1A:
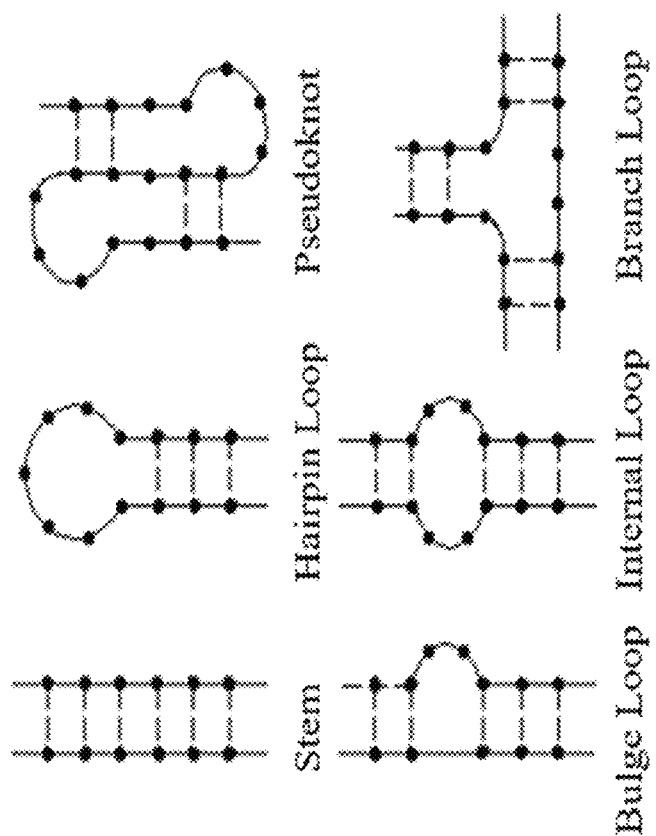
FIG. 1A illustrates RNA structures that can be used in gRNA extensions.

Provided herein are structure-engineered guide RNA (gRNA) molecules, including structure-engineered crRNA and/or tracrRNA as well as single-guide (sgRNA) molecules, useful in CRISPR/Cas gene editing systems. The structure-engineered gRNA comprising an extension sequence of about 8 nucleotides or more, particularly an extension sequence that self-hybridizes to form a structured RNA extension.

Guide RNA

A guide RNA, as used herein, is a nucleic acid molecule that binds to an RNA-guided endonuclease (e.g., Cas9) and targets the modified RNA-guided endonuclease to a specific location within a target nucleic acid to be edited. Any suitable guide nucleic acid can be used in accordance with the invention. Guide nucleic acids suitable for inclusion in a complex of the present disclosure include any guide nucleic acid from any CRISPR system, including single-molecule guide nucleic acids ("single-guide RNA"/ "sgRNA") and dual-molecule guide nucleic acids ("dual-guide RNA"/"dgRNA").

A guide RNA comprises at least two segments, a first segment referred to as a "targeting segment" and a second segment referred to as a "protein-binding segment."

The targeting segment of the gRNA interacts with a target nucleic acid to be edited (e.g., a target nucleic acid in a cell) in a sequence-specific manner via hybridization (i.e., base pairing). Thus, the targeting segment comprises a stretch of nucleotides with a sequence that is sufficiently complementary to the target site to be edited to allow hybridization. The targeting sequence can be engineered to hybridize to any desired target site in the nucleic acid to be edited. Accordingly, nucleotide sequence of the targeting segment depends on the sequence of the target gene to be edited.

The targeting segment typically has a length of about 12 nt or more, such as about 15 nt or more, 17 nt or more, 18 nt or more, 19 nt or more, 20 nt or more, 25 nt or more, 30 nt or more, 35 nt or more or 40 nt. For example, the targeting segment can have a length of from 12 nt to 80 nt, from 12 nt to 50nt, from 12 nt to 40 nt, from 12 nt to 30 nt, from 12 nt to 25 nt, from 12 nt to 20 nt, or from 12 nt to 19 nt. For example, the targeting segment can have a length of from 17 nt to 20 nt, from 17 nt to 25 nt, from 17 nt to 30 nt, from 17 nt to 35 nt, from 17 nt to 40 nt, from 17 nt to 45 nt, from 17 nt to 50 nt, from 17 nt to 60 nt, from 17 nt to 70 nt, from 17 nt to 80 nt, from 17 nt to 90 nt, 18 nt to 20 nt, from 18 nt to 25 nt, from 18 nt to 30 nt, from 18 nt to 35 nt, from 18 nt to 40nt, from 18 nt to 45 nt, from 18 nt to 50 nt, from 18 nt to 60 nt, from 18 nt to 70 nt, from 18 nt to 80 nt, from 18 nt to 90 nt, 19 nt to 20 nt, from 19 nt to 25 nt, from 19 nt to 30 nt, from 19 nt to 35 nt, from 19 nt to 40 nt, from 19 nt to 45 nt, from 19 nt to 50 nt, from 19 nt to 60 nt, from 19 nt to 70 nt, from 19 nt to 80 nt, from 19 nt to 90 nt, from 19 nt to 100 nt, from 20 nt to 25 nt, from 20 nt to 30 nt, from 20 nt to 35 nt, from 20 nt to 40 nt, from 20 nt to 45 nt, from 20 nt to 50 nt, from 20 nt to 60 nt, from 20 nt to 70 nt, from 20 nt to 80 nt, from 20 nt to 90 nt, or from 20 nt to 100 nt.

The targeting sequence (i.e., guide sequence) of the targeting segment must be sufficiently complementary to the target site of the target nucleic acid to allow hybridization. The targeting sequence can be, for instance, 60% or more (e.g., 65% or more, 70% or more, 75% or more, 80% or more, 85% or more, 90% or more, 95% or more, 97% or more, 98% or more, 99% or more, or 100%). In some embodiments, the targeting sequence comprises a "seed" region of at least six or seven nucleotides (e.g., 8, 9, 10, 11, or 12 nt) that binds the region of target sequence proximal (closest) to the PAM site for the system being used, and the percent complementarity between the seed region of the targeting sequence of the targeting segment and the target site of the target nucleic acid is at least about 99%, 99.5%, or even 100% (e.g., at least about 99%, 99.5%, or even 100% complementarity over the at least six or seven contiguous 5'-most nucleotides of the target site of the target nucleic acid (3'-most nucleotides of the targeting sequence in the gRNA) in the case of a Cas9 guide nucleic acid).

The protein-binding segment of a gRNA interacts with the RNA-guided endonuclease protein. The particular sequence of the protein-binding segment will depend upon the RNA-guided endonuclease of the particular CRISPR system to be used. However, the protein binding segment of a gRNA typically comprises two stretches of nucleotides that are complementary to one another and hybridize to form a double stranded RNA duplex (dsRNA) region that generally forms a stem structure. The dsRNA duplex of the protein-binding segment can have any length, which might vary depending on the CRISPR system being used, but is typically from about 6 bp to about 50 bp. The two strands of the hybridized double-stranded RNA segment are sufficiently complementary to allow hybridization, but need not be 100% complementary (e.g., they may be 65% or more, 70% or more, 75% or more, 80% or more, 85% or more, 90% or more, 95% or more, 98% or more, or 99% or more complementary to one another). The dsRNA sometimes contains an intervening non-hybridized region that forms a bulge dividing the stem into an upper stem and lower stem. The protein binding region may comprise additional regions that are complementary to one another and self-hybridize to form additional structures (e.g., one or more hairpin loops, stems, bulges, and/or a *nexus*). The particular sequences and structures of the protein-binding segment will depend upon the particular CRISPR/Cas system being used (e.g., the particular RNA-guided endonuclease protein that will be used with the guide RNA).

In some embodiments, the guide RNA comprises two separate nucleic acid molecules that hybridize to one another to provide the guide RNA. Guide RNA of this type is typically referred to as dual-guide RNA (dgRNA). The hybridized region between the two nucleic acids provides a dsRNA duplex stem structure as described above. Thus, one nucleic acid typically comprises the targeting sequence and one strand of the dsRNA region that joins the two nucleic acids, and the other nucleic acid comprises the second strand of the dsRNA region along with the remaining portions of the protein-binding region. The nucleic acid comprising the targeting segment and of the two dsRNA hybridizing strands is often referred to as crRNA. The nucleic acid comprising the other strand of the dsRNA region and the remaining portion of protein binding segment is often referred to as tracrRNA. Typically, the crRNA comprises a targeting sequence at the 5' end, and the segment complementary with the tracrRNA at the 3' end, while the tracrRNA comprises the segment complementary with the crRNA at the 5' end. The crRNA and tracrRNA can have any suitable length, which will depend at least in part on the particular CRISPR system being used (e.g., the particular RNA-guided endonuclease that must recognize the gRNA). In some embodiments, the crRNA comprises about 30 or more nt (e.g., 40 or more, 50 or more, 60 or more, 70 or more, 75 or more nt). In some embodiments, the tracrRNA has a length in a range of about 30-200 nt.

When the gRNA comprises the targeting segment and protein-binding segment in the same nucleic acid, the gRNA may be referred to as a single guide RNA (sgRNA). sgRNA can be created from two separate nucleic acids of a dual-guide RNA system, for instance, by linking the nucleic acid comprising the targeting sequence (e.g., crRNA) to the nucleic acid comprising the protein-binding segments (e.g., tracrRNA) (e.g., linking the 3' end of the crRNA to the 5' end of the tracrRNA by way of a linker sequence), provided the linker does not substantially interfere with the sgRNA from interacting with the RNA guided endonuclease and the target nucleic acid to be edited. The linker also should allow the crRNA to hybridize to the tracrRNA in a manner that allows formation of the dsRNA stem structure described with respect to the dual guide RNA. The linker is not particularly limited to any particular length, but typically will comprise about 3-10 nt, such as about 3-5 nt (e.g., about 4 nt). Suitable inker sequences are known in the art.

In some embodiments, the guide RNA can be a DNA/RNA hybrid molecule. For instance, the protein binding segment of the guide RNA can comprise RNA, while the targeting segment can comprise DNA, or both RNA and DNA.

Exemplary guide RNA molecules include those for CRISPR Type II systems, such as Cas9. Cas9 guide nucleic acids useful in the invention include any guide nucleic acid with a protein binding domain (e.g., tracrRNA) that binds to any Cas9 ortholog or variant, as described herein with respect to the Crisper Systems, below. Many Cas9 orthologs are known in the art, including, for instance, *Streptococcus pyogenes, Legionella pneumophila, Gamma proteobacterium, Listeria innocus, Lactobacillus gasseri, Eubacterium* rectal, *Syaphylococcus lugdunensis, Mycoplasma synoviae, Mycoplasma mobile, Wolinella succinogenes, Flavobacetrium columnare, Fibrobacter succinogenes, Bacteroides fragilis, Acidothermus cellulolyticus, Bifidobacterium dentium, Francisella tularensis* (e.g., subsp. *Novicida*), *Pasteurella multocida, Neisseria meningitidis, Campylobacter jejuni, Streptococcus thermophilus* (e.g. *Streptococcus thermophilus* #1, or *Streptococcus thermophilus* LMD-9 CRISPR 3), *Campylobacter lari* (e.g., *Campylobacter lari* CF89-12), *Mycoplasma gallisepticum* (e.g., str. F), *Nitratifractor salsuginis* (e.g., str DSM 16511), *Parvibaculum lavamentivorans, Roseburia intestinalis, Neisseria cinerea, Gluconacetobacter diazotrophicus, Azospirillum* B510, *Sphaerochaeta globus* (e.g., str. Buddy), *Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pseudintermedius, Filifactor alocis, Treponema denticola, Legionella pneumophila* (e.g., str. Paris), *Sutterella wadsworthensis, Corynebacter diphtheriae*, and *Staphylococcus aureus*, among others. Additional Cas9 orthologs can be identified using available techniques and tools. Orthogonal Cas9 proteins can be selected by examining and identifying divergent repeat sequences. Tools like CRISPRfinder (Grissa et al., *Nucleic Acids Res* 35: W52-W57 (2007), and CRISPRdb (Grissa et al., *BMC Bioinformatics* 8: 172 (2007) enable identification of CRISPR arrays with their constituent spacer and repeat sequences.

Thus, the protein binding segment (e.g., tracrRNA) used in accordance with the invention can comprising any tracrRNA of the foregoing microorganisms, or a variant thereof that retains the ability to bind a Cas9 protein. More specific examples of protein binding segments (e.g., tracrRNA) include those comprising any of SEQ ID NOs: 6-30, or a variant thereof that retains the function of binding a Cas9 polypeptide. Variants can comprise, for instance, at least 60%, 65%, 70%, 75%, 80%, 85%, 90%, or 95% sequence identity to SEQ ID NOs: 6-30 (e.g., SEQ ID NOs: 6-30 with 1, 2, 3, 4, 5, 6, 7, 8, 9, 10, 11, 12, 13, 14, or 15 nucleotide substitutions, additions, or deletions). Similarly, the guide RNA can be any guide RNA comprising such a protein binding segment (e.g., tracrRNA).

In other embodiments, a suitable protein binding segment (e.g., tracrRNA) comprises a nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any guide RNA or protein binding segment thereof set forth in International Patent Application No. PCT/US2016/052690, or a complement thereof.

A guide RNA comprising any of the foregoing exemplary protein binding segments (e.g., tracrRNAs) will include a targeting segment (crRNA) with a region that hybridizes to the protein binding segment and provides a dsRNA region, typically in a stem-like structure. Thus, the targeting segment can comprise, for instance, a region of at least about 6 bp (e.g., 6-50 bp) that is at least about 60% or more (e.g., 65% or more, 70% or more, 75% or more, 80% or more, 85% or more, 90% or more, 95% or more, 98% or more, 99% or more, or 100%) complementary to a corresponding region of the protein binding segment. For illustration, in some embodiments, the targeting segment can comprise a nucleotide sequence having 60% or more (e.g., 65% or more, 70% or more, 75% or more, 80% or more, 85% or more, 90% or more, 95% or more, 98% or more, 99% or more, or 100%) nucleotide sequence identity over a stretch of 8 or more contiguous nucleotides (e.g., 8 or more contiguous nucleotides, 10 or more contiguous nucleotides, 12 or more contiguous nucleotides, 15 or more contiguous nucleotides, or 20 or more contiguous nucleotides) to any one of the foregoing protein binding segments. The remaining portion of the targeting segment includes the targeting sequence the nucleic acid sequence of the targeting segment (e.g., crRNA) of the guide RNA will depend upon the target sequence to be edited.

The protein binding segment, targeting segment, or both can be further modified in any manner known in the art. For instance, any portion of the guide RNA can comprise modified internucleotide linkages such as, for example, phosphorothioates, phosphoramidates, and O-methyl ribose or deoxyribose residue.

Structure-Engineered Extensions

The guide RNA or portion thereof (e.g., crRNA or tracrRNA) provided herein comprises an extension sequence. The extension can be present at any end or terminus of the crRNA, tracrRNA, or guide RNA comprising same. Furthermore, the extension sequence can comprise RNA, DNA, or a combination thereof.

Figure 1B:
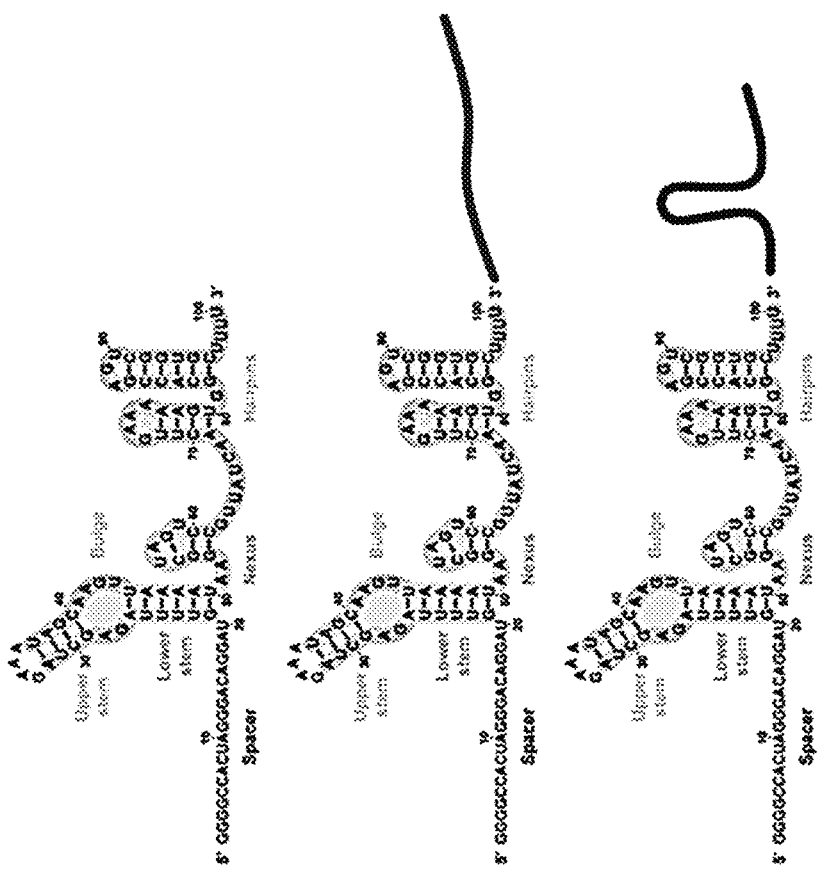
FIG. 1B shows a general schematic of gRNA extensions (gRNA SEQ ID NO: 48).
Figure 1C:
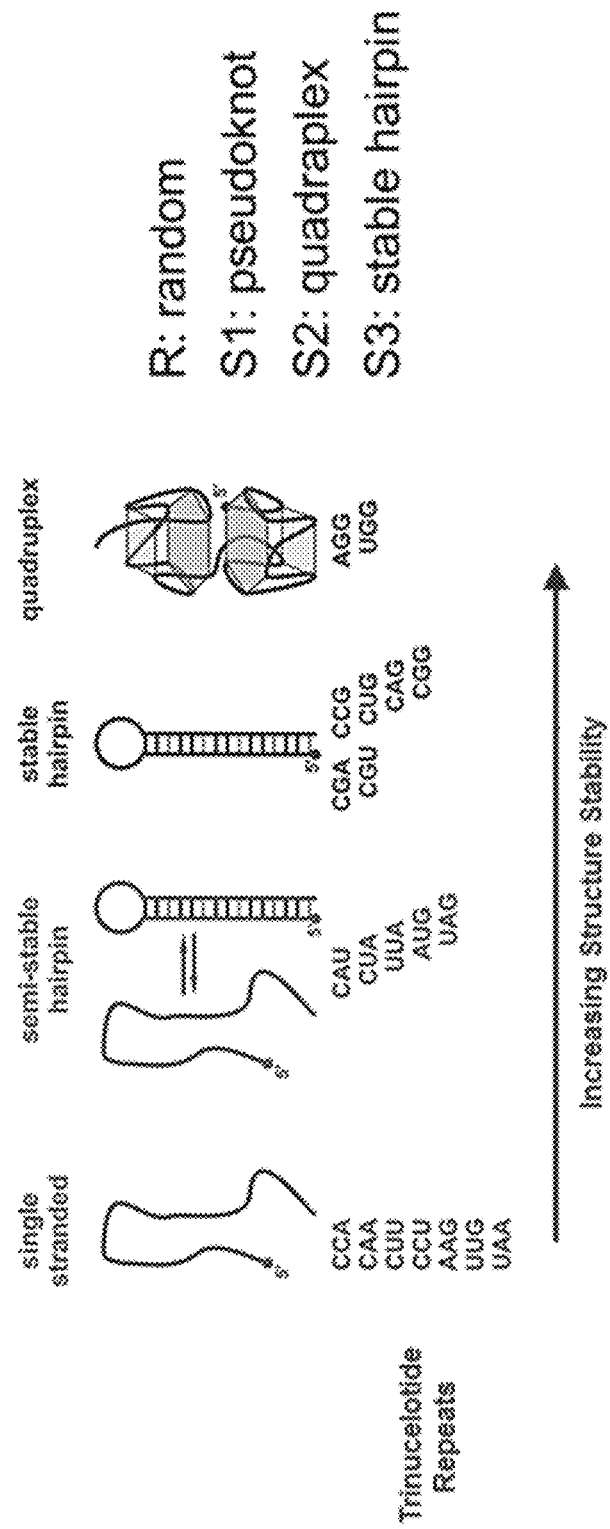
FIG. 1C illustrates trinucleotide repeats that can be used to provide various RNA structures.

In one aspect, there is provided a tracrRNA comprising the extension sequence, as well as a guide RNA comprising the tracrRNA and a crRNA. According to one embodiment, the extension sequence is at the end of the tracrRNA, and the tracrRNA is, optionally, part of a guide RNA. The extension sequence is at the end of the tracrRNA opposite the segment of the tracrRNA that hybridizes to the crRNA when present to provide a guide RNA (e.g., the 3' end of the tracrRNA in a Type II CRISPR/Cas9 system). The guide RNA, according to an embodiment, comprises the extended tracrRNA and a crRNA hybridized to the tracrRNA (e.g., 5' end region of the tracrRNA is hybridized to the 3' end region of the crRNA). The guide RNA may be a dual guide RNA, wherein the tracrRNA and crRNA are hybridized but not covalently linked, or a single guide RNA in which the tracrRNA and crRNA are hybridized as well as covalently linked (e.g., 5' terminus of the tracrRNA is linked to the 3' terminus of the crRNA. FIG. 1B illustrates the placement of an extension sequence at the 3' end of the protein binding segment (tracrRNA) of a Cas9 single guide RNA.

In another embodiment, the tracrRNA comprises the extension sequence on the same end of the tracrRNA that hybridizes to the crRNA when present to provide a guide RNA (e.g., the 5' end of the tracrRNA in a Type II CRISPR/Cas9 system), provided that the extension does not interfere with hybridization to a corresponding crRNA or interaction with the RNA guided endonuclease. In this embodiment, the tracrRNA can be part of a guide RNA comprising crRNA hybridized to the tracrRNA (e.g., dual guide RNA).

In yet another embodiment, the crRNA comprises an extension at the 3' end or 5' end of the crRNA, provided that, when extended on the end of the crRNA that hybridizes with a tracrRNA to provide a guide RNA, the extension does not interfere with the hybridization or with interaction of a guide RNA with the RNA guided endonuclease.

The extension sequence is a nucleotide sequence that generally comprises at least about 8 nt. In some embodiments, the extension sequence comprises about 10 nt or more, about 15 nt or more, about 20 nt or more, about 25 nt more, about 30 nt or more, about 35 nt or more, about 40 nt or more, about 45 nt or more, or about 50 nt or more. In other embodiments, the extension comprises about 75 nt or more, or even 100 nt or more. There is no upper limit on the length or number of nucleotides of the extension. In some embodiments, the extension comprises less than about 1000 nt (e.g., less than about 750 nt or less than about 500 nt).

In some embodiments, the extension self-folds (self-hybridizes) to provide a structured extension. There is no limitation on the type of structure provided. The extension can have a random coil structure; however, in some embodiments, the extension has a structure that is more compact than a random coil structure of the same number of nucleotides, which provides a greater negative charge density. By increasing the overall length of the extension, the negative charge of the molecule is increased. When a more compact structure is used, the overall negative charge density of the molecule is further increased. Compactness or charge density can be determined according to mobility in gel electrophoresis. More particularly, if gel electrophoresis is performed for two nucleic acids with the same number of nucleotides run together on the same gel, the nucleic acid with the higher mobility (moves farthest in the gel) is deemed to have a more compact structure.

In another embodiment, the extension sequence comprises at least one semi-stable hairpin structure, stable hairpin structure, pseudoknot structure, G-quadraplex structure, bulge loop structure, internal loop structure, branch loop structure, or a combination thereof. These types of nucleotide structures are known in the art and schematically illustrated in FIG. 1A. It is to be understood that the illustrations are merely for the purpose of illustrating the general structure, and is not intended to be a detailed illustration of the actual molecular structure. Those of skill in the art recognize that a hairpin structure, for instance, can have interspersed regions of non-complementarity that produce "bulges" or other variations in the structure, and that the other depicted structures can include similar variations. The structure of a given nucleotide sequence can be determined using available algorithms (e.g., "The mfold Web Server" operated by Rensselaer Polytechnic Institute and The RNA Institute, College of Arts and Sciences, State University of New York at Albany; see also M. Zuker, D. H. Mathews & D. H. Turner. Algorithms and Thermodynamics for RNA Secondary Structure Prediction: A Practical Guide In *RNA Biochemistry and Biotechnology*, 11-43, J. Barciszewski and B. F. C. Clark, eds., NATO ASI Series, Kluwer Academic Publishers, Dordrecht, NL, (1999)).

The type of structure provided can be controlled using a repeating trinucleotide motif. A repeating trinucleotide motif is a motif of three nucleotides that is repeated in the sequence at least twice (e.g., repeated two or more times, three or more times, four or more times, five or more times, six or more times, seven or more times, eight or more times, or ten or more times). Thus, the extension sequence can comprise a repeating trinucleotide motif. In one embodiment, the extension sequence comprises a repeating trinucleotide motif of CAA, UUG, AAG, CUU, CCU, CCA, UAA, or a combination thereof, which provides a random coil sequence. In another embodiment, the extension sequence comprises a repeating trinucleotide motif of CAU, CUA, UUA, AUG, UAG, or a combination thereof, which provides a semi-stable hairpin structure. In another embodiment, the extension sequence comprises a repeating CNG trinucleotide motif (e.g., CGG, CAG, CUG, CCG), a repeating trinucleotide motif of CGA or CGU, or a combination thereof, which provides a stable hairpin structure. In another embodiment, the extension sequence comprises a repeating trinucleotide motif of AGG, UGG, or combination thereof, which provides a quadruplex (or G-quadruplex) structure. In yet another embodiment, the extension sequence comprises a combination of the foregoing trinucleotide motifs and a combination of the different structures thereby produced. For instance, the extension sequence could have a region comprising a random coil structure, a region comprising a semi-stable hairpin, a region comprising a stable hairpin, and/or a region comprising a quadruplex. Each region might, thus, comprise the repeating trinucleotide motif associated with the indicated structure. Non-limiting examples of extensions are those comprising SEQ ID NOs: 31-37.

Although the modified tracrRNA must be used with a targeting segment (crRNA) to direct gene editing at a target location, the modified tracrRNA is useful as an intermediate in the production of guide RNA, as the same tracrRNA modified with an extension as provided herein can be produced in bulk and used in conjunction with various different crRNA molecules tailored to desired target sites.

In some embodiments, the extension sequence provides additional functions. For instance, the extension sequence can hybridize to other nucleic acid sequences, for instance, a donor nucleic acid. The extension sequence also can be used to create guide RNA multimers; thus, in another embodiment, there is provided a guide RNA multimer (e.g., an sgRNA multimer) comprising two or more gRNA molecules (e.g., 3 or more, 4 or more, 5 or more, 6 or more, 7 or more, or even 8 or more gRNA molecules), wherein each guide RNA comprises an extension sequence as described herein, and the gRNA molecules of the multimer are joined by their extension sequences, for instance, through base pairing or hybridization. Thus, in one embodiment, each gRNA of the multimer comprises an extension sequence comprising a region sufficiently complimentary to a region of an extension of another gRNA of the multimer to facilitate hybridization. The complimentary region can be of any suitable length to facilitate the interaction (e.g., 4 nt or more, 6 nt or more, 8 nt or more, 10 nt or more, 15 nt or more, etc.). Guide RNA multimers are useful, for example, to deliver multiple sgRNAs simultaneously, such as when multiple sgRNAs are desired for particular therapeutic strategies. One example of such a use is exon skipping, in which a DNA fragment is cleaved by two sgRNAs to restore the functional reading frame (e.g., Ousterout D G, et al. (2015) Multiplex CRISPR/Cas9-based genome editing for correction of dystrophin mutations that cause Duchenne Muscular Dystrophy. *Nat Commun.* 6:6244). Exon skipping requires two sgRNAs each targeting a different site (one at the 5'-site and the other at the 3'-site) in the nucleus for targeting. Ideally, the ratio of two sgRNAs should be 1 to 1; however, it is difficult to maintain this ratio. By pairing sgRNAs (e.g., each comprising different targeting sequences) in multimers through appropriate extension structures, delivery in the desired ratio can be facilitated.

Figure 1D:
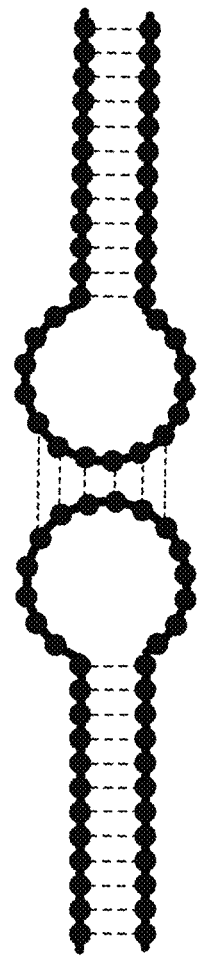
FIG. 1D illustrates the intersection of hybridizing extension sequences of sgRNA in a kissing loop, which can be used to form gRNA multimers.

In one embodiment, two or more guide RNAs with structured extensions engage in an RNA "kissing" interaction (a.k.a. loop-loop interaction), which occurs when the unpaired nucleotides in one structured extension sequence (e.g., a hairpin loop), base pair with the unpaired nucleotides in another structure (e.g., another hairpin loop) on a second gRNA. An example of this type of interaction is illustrated FIG. 1D. The formation of kissing loops or other structures multimerizes the two or more gRNA molecules. This strategy can be applied to link several gRNA molecules.

Figure 1E:
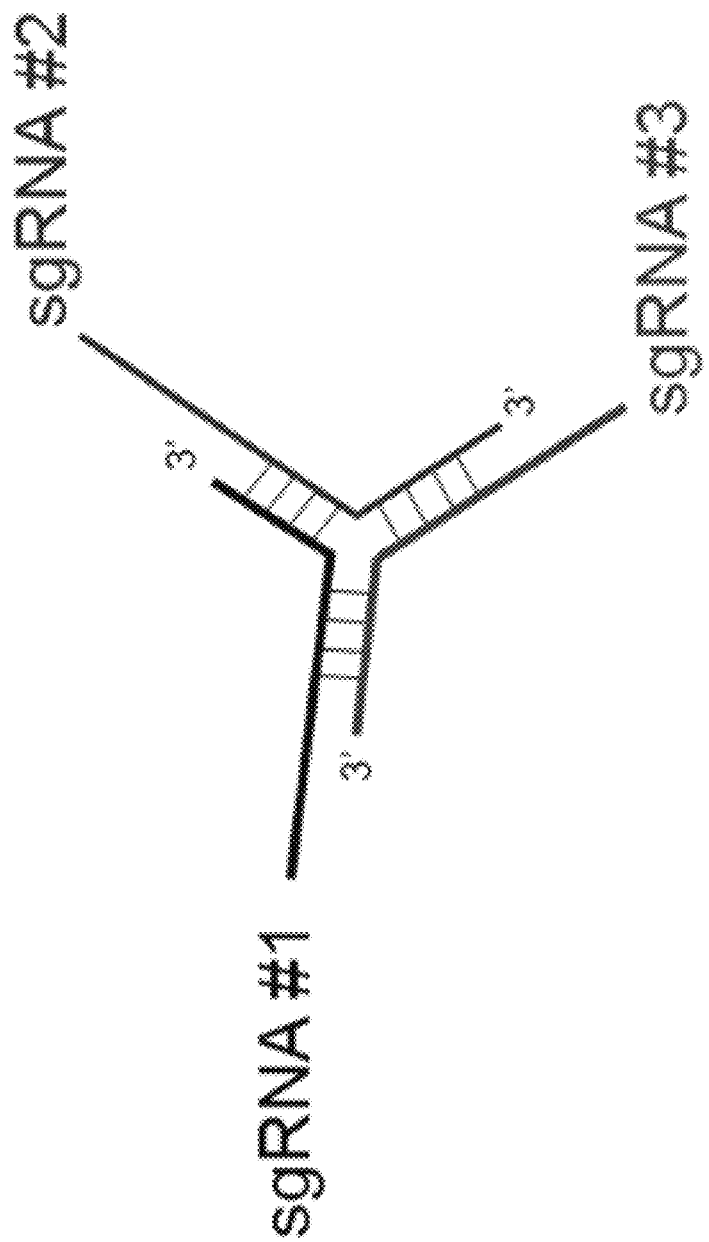
FIG. 1E illustrates the intersection of hybridizing extension sequences of gRNA to form trimers.

Hybridization of complementary sequences in the extension on each sgRNA also can be used to facilitate multimerization. For instance, supermolecular sgRNA structures can be constructed via the extended regions that have capability of self-assembly. For example, a trimer can be formed by three RNA molecules with appropriately placed hybridization regions (e.g., FIG. 1E; Shu D, Shu Y, Haque F, Abdelmawla S, & Guo P (2011) Thermodynamically stable RNA three-way junctions as platform for constructing multi-functional nanoparticles for delivery of therapeutics. *Nat Nanotechnol.* 6(10):658-667)). Similarly, a RNA octamer could be generated by assembling sixteen RNA molecules (Yu J, Liu Z, Jiang W, Wang G, & Mao C (2014) De novo design of an RNA tile that self-assembles into a homo-octameric nanoprism. *Nat Commun.* 6:5724)).

Figure 1F:
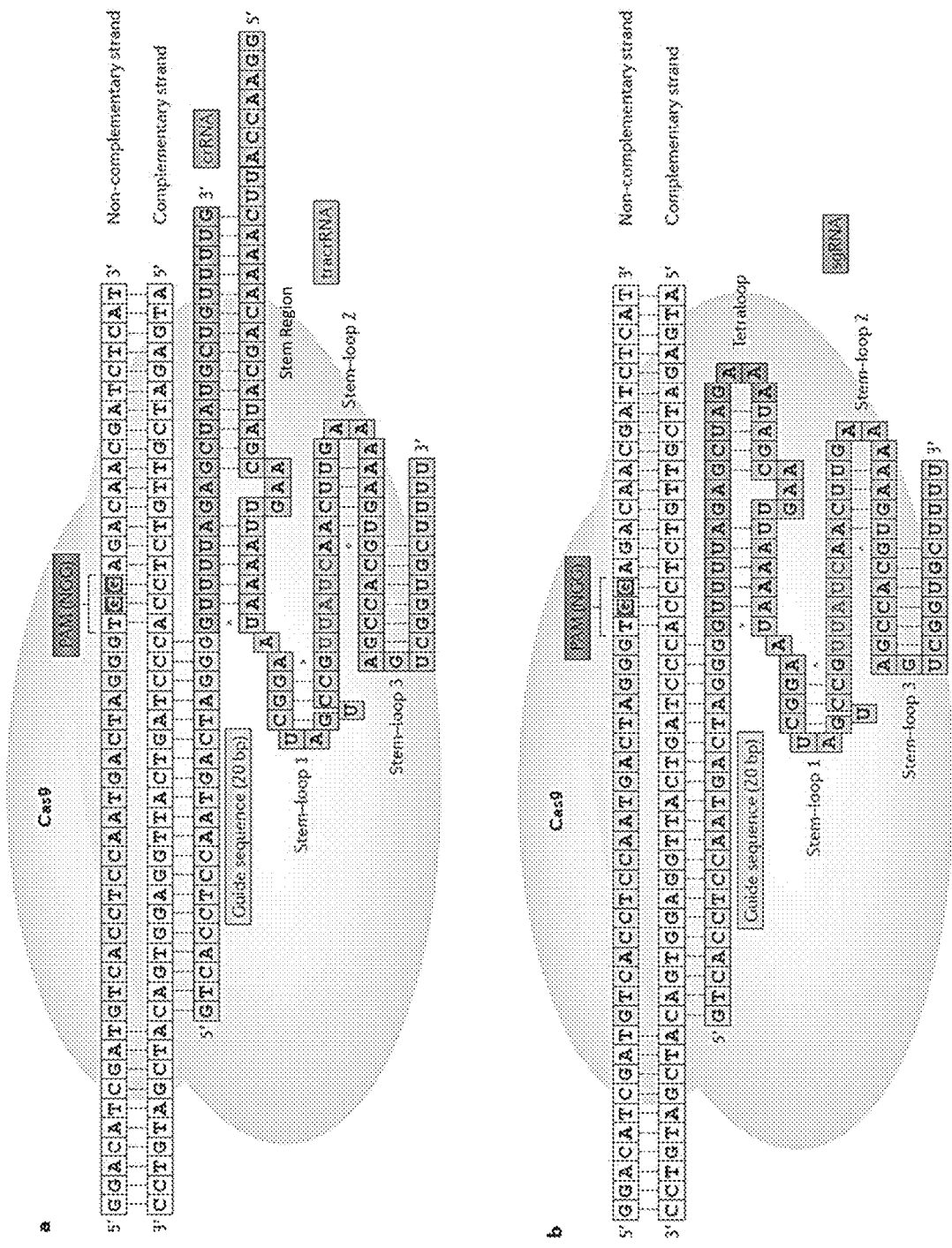
FIG. 1F illustrates the general structure of a Cas9 dual guide RNA (crRNA and tracrRNA; panel (a)) and single guide RNA (panel (b)), wherein the illustration shows in panel (a) a non-complementary strand (SEQ ID NO: 49), complementary strand (SEQ ID NO: 50), crRNA (SEQ ID NO: 51), and tracrRNA (SEQ ID NO: 52), and in panel (b) a non-complementary strand (SEQ ID NO: 49), complementary strand (SEQ ID NO: 50), and a single guide RNA (SEQ ID NO: 53).

The gRNA provided herein also can be comprise an extension sequence at an internal location in addition, or instead, of an extension at a terminus of the gRNA or component thereof. For instance, it was previously explained that the target binding segment (e.g., crRNA) and protein binding segment (e.g., tracrRNA) of a gRNA have complementary regions that hybridize to a stem structure (see, e.g., FIG. 1F, region referenced as "stem"). In sgRNA, this stem structure can be connected by a linker to form what is sometimes referred to as a tetra loop region (FIG. 1F). The extension sequence can be located at the end of the stem structure, either at the end of the 3' end of the target binding segment (e.g., crRNA), or at the 5' end of the protein binding segment (e.g., tracrRNA). Furthermore, the extension can join the 3' end of the target binding segment (e.g., crRNA) and the 5' end of the protein binding segment (e.g., tracrRNA) so as to provide an sgRNA. The extension can be any extension sequence as described herein. Alternatively, or in addition, the gRNA can comprise an extension sequence of Stem-Loop 2 (see FIG. 1F). For example the "GAAA" terminus of Stem-Loop 2 can be replaced by an extension sequence (e.g., greater than 4 nt), which optionally forms a longer stem loop.

In one embodiment, there is provided a gRNA multimer comprising two or more gRNA each comprising an extension sequence at an internal location as described above, wherein the extension sequence forms a stem-loop structure and each loop of the stem loop structure comprises a region that is complementary to the that of another gRNA in the multimer, such that the gRNA units of the multimer are bound though hybridization of "kissing loops."

In some embodiments, the extension sequence can comprise an aptamer sequence. However, it is often not desirable to recruit binding of proteins other than the RNA-guided endonuclease to the guide RNA. Furthermore, aptamer sequences typically have complex folding patterns that can be bulky and not compact. Thus, in other embodiments, the extension sequence is not an aptamer sequence.

The extension sequence can further comprise chemical modifications. For instance, the extension can comprise modified internucleotide linkages. Examples of modified internucleotide linkages include, without limitation, phosphorothioate, phosphorodithioate, methylphosphonate, phosphoramidate, 2'-O-methyl, 2'-O-methoxyethyl, 2'-fluoro, bridged nucleic acid (BNA), or phosphotriester modified bonds, as well as combinations thereof. The extension sequence or some portion thereof also can comprise synthetic nucleotides, such as xeno nucleic acids (XNAs) that are resistant to nucleases. XNAs are nucleic acids in which the ribofuranose ring of DNA or RNA is replaced by five- or six-membered modified ribose molecules, such as 1,5 anhydrohexitol nucleic acids (HNAs), cyclohexenyl nucleic acids (CeNAs), and 2'4'-C—(N-methylaminomethylene) bridged nucleic acids (BNAs), 2'-O,4'-C-methylene-β-D-ribonucleic acids or locked nucleic acids (LNAs), ANA (arabinonucleic acids), 2'-fluoro-arabinonucleic acid (FANAs) and α-L-threofuranosyl nucleic acids (TNAs).

Furthermore, any combination thereof also can be used. The extension sequence also can comprise chemical modifications at the free terminus thereof (i.e., the end of the extension sequence that is not attached to the guide RNA). For instance, the terminus of the extension can be modified with a functional group that provides convenient attachment of another biofunctional molecule, such as a functional group that facilitates a bioorthogonal or "click" chemical reaction. In some embodiments, the group attached to the free terminus of the extension is an azide, a tetrazine, alkyne, strained alkene, or strained alkyne allowing for the convenient attachment of a biofunctional molecule containing, or modified to contain, an appropriately paired functional group. For instance, an azide will react with an alkyne group of another biofunctional molecule via azide-alkyne cycloaddition (copper catalyzed), or will react with a strained alkyne group of a biofunctional molecule via azide-strained alkyne cycloaddition (no catalyst required). Likewise, a tetrazine will react with a strained strained alkene via tetrazine/alkene cycloaddition. Similarly, the opposite configuration can be used, e.g., an alkyne, strained alkyne, or strained alkene on the extension will react with an azide or a tetrazine group of a biofunctional molecule by the same cycloaddition reaction. Other paired functional groups include those comprising a thiol and alkene, which participate in thiol-ene reaction.

The added functional group can be unattached, providing an extension that is ready to be attached to a biofunctional molecule, or it can be attached to a biofunctional molecule. When attached to the biofunctional molecule via one of the above chemistries, the resulting molecule will comprise the extension and biofunctional molecule attached via the resulting linkage, e.g., for instance, a triazole group or a cyclic alkene group (i.e., a linkage comprising a triazole or cyclic alkene moiety) or an alkyl sulfide as resulting from thiol-ene chemistry. Of course, the foregoing linkages are only illustrative, and the extension sequence can comprise a biofunctional molecule attached to the free terminus thereof via any chemistry/any linkage suitable for the task, many of which are known in the art.

The biofunctional molecule chosen will depend upon the desired end use. By way of examples, molecules that enhance the delivery or activity of the guide RNA or RNA-guided endonuclease can be used, or molecules that facilitate the detection or monitoring of the delivery or activity of the guide RNA or RNA-guided endonuclease. Examples of biofunctional molecules include, for instance, endosomolytic polymers, donor DNA molecules, amino sugars (e.g., N-acetylgalatosamine (GalNAc) or tri-GalNAc), detectable labels (e.g., fluorescent markers, radiolabels, etc.) as well as other peptides, nucleic acids, and targeting ligands (e.g., antibodies, ligands, cell receptors, aptamers, galactose, sugars, small molecules).

The tracrRNA, crRNA, and guide RNA modified with an extension sequence can be provided by prepared by any suitable technique, including well known recombinant methods as well as nucleic acid synthesis (e.g., solid-phase synthesis). In some embodiments, the extension sequence is contiguous with the guide RNA sequence (e.g., same backbone chemistry attaching the extension sequence to the guide RNA). In other embodiments, the extension sequence is attached to the guide RNA via a different chemistry, such as by way of the biorthogonal or "click" chemistry linkages described above with respect to the attachment of other biofunctional molecules.

Compositions

Further provided herein is a composition comprising the modified guide RNA, or tracrRNA or crRNA thereof, described herein, and a carrier or vehicle. The guide RNA can be in the form of a guide RNA multimer as described herein. The vehicle or carrier can be any vehicle or carrier of the type typically used to store and/or deliver nucleic acids. The composition can further comprise other elements of the CRISPR system in which the guide RNA is intended to be used, for example, a RNA-guided endonuclease protein or nucleic acid (e.g., vector or mRNA) encoding same and, optionally, a donor nucleic acid. The guide RNA and other components of the CRISPR system in the composition are sometimes referred to herein as the "CRISPR complex" or simply the "complex."

RNA-Guided Endonuclease or Nucleic Acid Encoding Same

The composition can comprise any RNA-guided endonuclease or nucleic acid (e.g., vector or mRNA) encoding same that can be expressed after deliver to a cell to provide the RNA guided endonuclease protein. The RNA-guided endonuclease used will be appropriately paired with the protein-binding segment of the guide RNA so that the polypeptide is guided by the guide RNA to the desired target site of a gene to be edited.

In one embodiment, the polypeptide is a Cas9 polypeptide. Suitable Cas9 polypeptides for inclusion in a complex of the present disclosure include naturally-occurring Cas9 polypeptides (e.g., naturally occurs in bacterial and/or archaeal cells), or non-naturally-occurring Cas9 polypeptides (e.g., the Cas9 polypeptide is a variant Cas9 polypeptide, a chimeric polypeptide, or the like), as described below. One skilled in the art can appreciate that the Cas9 polypeptide can be any variant derived or isolated from any source.

Many Cas9 orthologs are known in the art, including, for instance, *Streptococcus pyogenes, Legionella pneumophila, Gamma proteobacterium, Listeria innocus, Lactobacillus gasseri, Eubacterium rectal, Syaphylococcus lugdunensis, Mycoplasma synoviae, Mycoplasma mobile, Wolinella succinogenes, Flavobacetrium columnare, Fibrobacter succinogenes, Bacteroides fragilis, Acidothermus cellulolyticus, Bifidobacterium dentium, Francisella tularensis* (e.g., subsp. *Novicida*), *Pasteurella multocida, Neisseria meningitidis, Campylobacter jejuni, Streptococcus thermophilus* (e.g. *Streptococcus thermophilus* #1, or *Streptococcus thermophilus* LMD-9 CRISPR 3), *Campylobacter lari* (e.g., *Campylobacter lari* CF89-12), *Mycoplasma gallisepticum* (e.g., str. F), *Nitratifractor salsuginis* (e.g., str DSM 16511), *Parvibaculum lavamentivorans, Roseburia intestinalis, Neisseria cinerea, Gluconacetobacter diazotrophicus, Azospirillum B510, Sphaerochaeta globus* (e.g., str. Buddy), *Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pseudintermedius, Filifactor alocis, Treponema denticola, Legionella pneumophila* (e.g., str. Paris), *Sutterella wadsworthensis, Corynebacter diphtheriae,* and *Staphylococcus aureus,* among others. Additional Cas9 orthologs can be identified using available techniques and tools. Orthogonal Cas9 proteins can be selected by examining and identifying divergent repeat sequences. Tools like CRISPRfinder (Grissa et al., *Nucleic Acids Res* 35: W52-W57 (2007), and CRISPRdb (Grissa et al., *BMC Bioinformatics* 8: 172 (2007) enable identification of CRISPR arrays with their constituent spacer and repeat sequences.

The Cas9 protein also can be any variant of a naturally occurring Cas9 protein. For example, the Cas9 peptide of the present disclosure can include one or more of the mutations described in the literature, including but not limited to the functional mutations described in: Fonfara et al. Nucleic Acids Res. 2014 February; 42(4):2577-90; Nishimasu H. et al. Cell. 2014 Feb. 27; 156(5):935-49; Jinek M. et al. Science. 2012 337:816-21; and Jinek M. et al. Science. 2014 Mar. 14; 343(6176); Makarova et al., *Cell,* 168, DOI dx.doi.org.10.1016/j.cell.2016.12.038 (Jan. 12, 2017); see also U.S. patent application Ser. No. 13/842,859, filed Mar. 15, 2013, which is hereby incorporated by reference; further, see U.S. Pat. Nos. 8,697,359; 8,771,945; 8,795,965; 8,865,406; 8,871,445; 8,889,356; 8,895,308; 8,906,616; 8,932,814; 8,945,839; 8,993,233; and 8,999,641, the entire disclosures of which are hereby incorporated by reference.

In some embodiments, the systems and methods disclosed herein can be used with the wild type Cas9 protein having double-stranded nuclease activity. In other embodiments, a Cas9 mutant that act as a single stranded nickase, or other mutant with modified nuclease activity, is used. As such, a Cas9 polypeptide that is suitable for inclusion in a complex (e.g., an encapsulated complex) of the present disclosure can be an enzymatically active Cas9 polypeptide, e.g., can make single- or double-stranded breaks in a target nucleic acid, or alternatively can have reduced enzymatic activity compared to a wild-type Cas9 polypeptide. Binding assays and cleavage assays can be used to determine whether a given Cas9 polypeptide binds a given guide RNA and has nucleic acid cleavage activity.

Naturally occurring Cas9 polypeptides bind a guide nucleic acid, are thereby directed to a specific sequence within a target nucleic acid (a target site), and cleave the target nucleic acid (e.g., cleave dsDNA to generate a double strand break, cleave ssDNA, cleave ssRNA, etc.). A subject Cas9 polypeptide comprises two portions, an RNA-binding portion and an activity portion. The RNA-binding portion interacts with a subject guide nucleic acid, and an activity portion exhibits site-directed enzymatic activity (e.g., nuclease activity, activity for DNA and/or RNA methylation, activity for DNA and/or RNA cleavage, activity for histone acetylation, activity for histone methylation, activity for RNA modification, activity for RNA-binding, activity for RNA splicing etc. In some embodiments, the activity portion exhibits reduced nuclease activity relative to the corresponding portion of a wild type Cas9 polypeptide. In some embodiments, the activity portion is enzymatically inactive.

Assays to determine whether a protein has an RNA-binding portion that interacts with a subject guide nucleic acid can be any convenient binding assay that tests for binding between a protein and a nucleic acid. Exemplary binding assays include binding assays (e.g., gel shift assays) that involve adding a guide nucleic acid and a Cas9 polypeptide to a target nucleic acid.

Assays to determine whether a protein has an activity portion (e.g., to determine if the polypeptide has nuclease activity that cleave a target nucleic acid) can be any convenient nucleic acid cleavage assay that tests for nucleic acid cleavage. Exemplary cleavage assays that include adding a guide nucleic acid and a Cas9 polypeptide to a target nucleic acid.

In some embodiments, a suitable Cas9 polypeptide for inclusion in a complex of the present disclosure has enzymatic activity that modifies target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In other embodiments, a suitable Cas9 polypeptide for inclusion in a complex of the present disclosure has enzymatic activity that modifies a polypeptide (e.g., a histone) associated with target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Many Cas9 orthologues from a wide variety of species have been identified, as discussed above. In some instances, the orthologous proteins share only a few identical amino acids. Yet, most identified Cas9 orthologues have the same domain architecture with a central HNH endonuclease domain and a split RuvC/RNaseH domain. Cas9 proteins typically share 4 key motifs with a conserved architecture. Motifs 1, 2, and 4 are RuvC like motifs while motif 3 is an HNH-motif.

In some embodiments, a suitable Cas9 polypeptide comprises an amino acid sequence having 4 motifs (motifs 1-4), wherein each of motifs 1-4 having 60% or more, 70% or more, 75% or more, 80% or more, 85% or more, 90% or more, 95% or more, 99% or more or 100% amino acid sequence identity to the corresponding motif of the Cas9 amino acid sequence of SEQ ID NO:1; or, alternatively, to motifs 1-4 of the Cas9 amino acid sequence depicted in Table 1 below (motifs 1-4 of SEQ ID NO:1 are SEQ ID NOs: 3-6, respectively, as depicted in Table 1 below); or alternatively to amino acids 7-166 or 731-1003 of the Cas9 amino acid sequence of SEQ ID NO:1.

In some embodiments, a Cas9 polypeptide comprises an amino acid sequence having 75% or more, 80% or more, 85% or more, 90% or more, 95% or more, or 98%, amino acid sequence identity to the amino acid sequence of SEQ ID NO:1; and comprises amino acid substitutions of N497, R661, Q695, and Q926 relative to the amino acid sequence set forth in SEQ ID NO:1; or comprises an amino acid substitution of K855 relative to the amino acid sequence set forth in SEQ ID NO:1; or comprises amino acid substitutions of K810, K1003, and R1060 relative to the amino acid sequence set forth in SEQ ID NO:1; or comprises amino acid substitutions of K848, K1003, and R1060 relative to the amino acid sequence set forth in SEQ ID NO:1.

As used herein, the term "Cas9 polypeptide" encompasses the term "variant Cas9 polypeptide"; and the term "variant Cas9 polypeptide" encompasses the term "chimeric Cas9 polypeptide."

Variant Cas9 Polypeptides

A variant Cas9 polypeptide has an amino acid sequence that is different by one amino acid (e.g., has a deletion, insertion, substitution, fusion) (i.e., different by at least one amino acid) when compared to the amino acid sequence of a wild type Cas9 polypeptide (e.g., a naturally occurring Cas9 polypeptide, as described above). In some instances, the variant Cas9 polypeptide has an amino acid change (e.g., deletion, insertion, or substitution) that reduces the nuclease activity of the Cas9 polypeptide. For example, in some instances, the variant Cas9 polypeptide has less than 50%, less than 40%, less than 30%, less than 20%, less than 10%, less than 5%, or less than 1% of the nuclease activity of the corresponding wild-type Cas9 polypeptide. In some embodiments, the variant Cas9 polypeptide has no substantial nuclease activity. When a Cas9 polypeptide is a variant Cas9 polypeptide that has no substantial nuclease activity, it can be referred to as "dCas9."

In some embodiments, a variant Cas9 polypeptide has reduced nuclease activity. For example, a variant Cas9 polypeptide suitable for use in a binding method of the present disclosure exhibits less than about 20%, less than about 15%, less than about 10%, less than about 5%, less than about 1%, or less than about 0.1%, of the endonuclease activity of a wild-type Cas9 polypeptide, e.g., a wild-type Cas9 polypeptide of SEQ ID NO:1.

In some embodiments, a variant Cas9 polypeptide can cleave the complementary strand of a target nucleic acid but has reduced ability to cleave the non-complementary strand of a double stranded target nucleic acid. For example, the variant Cas9 polypeptide can have a mutation (amino acid substitution) that reduces the function of the RuvC domain. As a non-limiting example, in some embodiments, a variant Cas9 polypeptide has a D10A mutation (e.g., aspartate to alanine at an amino acid position corresponding to position 10 of SEQ ID NO:1) and can therefore cleave the complementary strand of a double stranded target nucleic acid but has reduced ability to cleave the non-complementary strand of a double stranded target nucleic acid (thus resulting in a single strand break (SSB) instead of a double strand break (DSB) when the variant Cas9 polypeptide cleaves a double stranded target nucleic acid) (see, for example, Jinek et al., Science. 2012 Aug. 17; 337(6096):816-21).

In some embodiments, a variant Cas9 polypeptide can cleave the non-complementary strand of a double stranded target nucleic acid but has reduced ability to cleave the complementary strand of the target nucleic acid. For example, the variant Cas9 polypeptide can have a mutation (amino acid substitution) that reduces the function of the HNH domain (RuvC/HNH/RuvC domain motifs, "domain 2"). As a non-limiting example, in some embodiments, the variant Cas9 polypeptide can have an H840A mutation (e.g., histidine to alanine at an amino acid position corresponding to position 840 of SEQ ID NO:1) and can therefore cleave the non-complementary strand of the target nucleic acid but has reduced ability to cleave the complementary strand of the target nucleic acid (thus resulting in a SSB instead of a DSB when the variant Cas9 polypeptide cleaves a double stranded target nucleic acid). Such a Cas9 polypeptide has a reduced ability to cleave a target nucleic acid (e.g., a single stranded target nucleic acid) but retains the ability to bind a target nucleic acid (e.g., a single-stranded or a double-stranded target nucleic acid).

In some embodiments, a variant Cas9 polypeptide has a reduced ability to cleave both the complementary and the non-complementary strands of a double stranded target nucleic acid. As a non-limiting example, in some embodiments, the variant Cas9 polypeptide harbors both the D10A and the H840A mutations (e.g., mutations in both the RuvC domain and the HNH domain) such that the polypeptide has a reduced ability to cleave both the complementary and the non-complementary strands of a double stranded target nucleic acid. Such a Cas9 polypeptide has a reduced ability to cleave a target nucleic acid (e.g., a single-stranded target nucleic acid or a double-stranded target nucleic acid) but retains the ability to bind a target nucleic acid (e.g., a single stranded target nucleic acid or a double-stranded target nucleic acid).

As another non-limiting example, in some embodiments, the variant Cas9 polypeptide harbors W476A and W1126A mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors P475A, W476A, N477A, D1125A, W1126A, and D1127A mutations such that the polypeptide has a reduced ability to cleave a target nucleic acid. Such a Cas9 polypeptide has a reduced ability to cleave a target nucleic acid but retains the ability to bind a target nucleic acid.

In some embodiments, a variant Cas9 polypeptide that has reduced catalytic activity (e.g., when a Cas9 protein has a D10, G12, G17, E762, H840, N854, N863, H982, H983, A984, D986, and/or a A987 mutation, e.g., D10A, G12A, G17A, E762A, H840A, N854A, N863A, H982A, H983A, A984A, and/or D986A), the variant Cas9 polypeptide can still bind to target nucleic acid in a site-specific manner (because it is still guided to a target nucleic acid sequence by a guide nucleic acid) as long as it retains the ability to interact with the guide nucleic acid.

TABLE 1

Table 1 lists 4 motifs that are present in Cas9 sequences from various species. The amino acids listed here are from the Cas9 from S. pyogenes (SEQ ID NO: 1).

| Motif | Motif | Amino acids (residue #s) | Highly conserved |
|---|---|---|---|
| 1 | RuvC | IGLDIGTNSVGWAVI (7-21) (SEQ ID NO: 2) | D10, G12, G17 |
| 2 | RuvC | IVIEMARE (759-766) (SEQ ID NO: 3) | E762 |
| 3 | HNH-motif | DVDHIVPQSFLKDDSIDNKVLTRSDKN (837-863) (SEQ ID NO: 4) | H840, N854, N863 |
| 4 | RuvC | HHAHDAYL (982-989) (SEQ ID NO: 5) | H982, H983, A984, D986, A987 |

As another non-limiting example, in some embodiments, the variant Cas9 polypeptide harbors H840A, W476A, and W1126A, mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors H840A, D10A, W476A, and W1126A, mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors, H840A, P475A, W476A, N477A, D1125A, W1126A, and D1127A mutations such that the polypeptide has a reduced ability to cleave a target nucleic acid. Such a Cas9 polypeptide has a reduced ability to cleave a target nucleic acid but retains the ability to bind a target nucleic acid.

As another non-limiting example, in some embodiments, the variant Cas9 polypeptide harbors D10A, H840A, P475A, W476A, N477A, D1125A, W1126A, and D1127A mutations such that the polypeptide has a reduced ability to cleave a target nucleic acid. Such a Cas9 polypeptide has a reduced ability to cleave a target nucleic acid but retains the ability to bind a target nucleic acid.

Other residues can be mutated to achieve the above effects (i.e. inactivate one or the other nuclease portions). As non-limiting examples, residues D10, G12, G17, E762, H840, N854, N863, H982, H983, A984, D986, and/or A987 can be altered (i.e., substituted) (see Table 1 for more information regarding the conservation of Cas9 amino acid residues). Also, mutations other than alanine substitutions are suitable.

In addition to the above, a variant Cas9 protein can have the same parameters for sequence identity as described above for Cas9 polypeptides. Thus, in some embodiments, a suitable variant Cas9 polypeptide comprises an amino acid sequence having 4 motifs, each of motifs 1-4 having 60% or more, 70% or more, 75% or more, 80% or more, 85% or more, 90% or more, 95% or more, 99% or more or 100% amino acid sequence identity of the Cas9 amino acid sequence of SEQ ID NO:1, or alternatively to motifs 1-4 (motifs 1-4 of SEQ ID NO:1 are SEQ ID NOs: 2-5, respectively, as depicted in Table 1); or alternatively to amino acids 7-166 or 731-1003 of the Cas9 amino acid sequence of SEQ ID NO:1. Any Cas9 protein as defined above can be used as a Cas9 polypeptide, or as part of a chimeric Cas9 polypeptide, in a complex of the present disclosure, including those specifically referenced in International Patent Application No. PCT/US2016/052690.

In some embodiments, a suitable variant Cas9 polypeptide comprises an amino acid sequence having 60% or more, 70% or more, 75% or more, 80% or more, 85% or more, 90% or more, 95% or more, 99% or more, or 100% amino acid sequence identity to the Cas9 amino acid sequence of SEQ ID NO:1. Any Cas9 protein as defined above can be used as a variant Cas9 polypeptide or as part of a chimeric variant Cas9 polypeptide in a complex of the present disclosure, including those specifically referenced in International Patent Application No. PCT/US2016/052690.

Chimeric Cas9 Polypeptides (Fusion Polypeptides)

In some embodiments, a variant Cas9 polypeptide is a chimeric Cas9 polypeptide (also referred to herein as a fusion polypeptide, e.g., a "Cas9 fusion polypeptide"). A Cas9 fusion polypeptide can bind and/or modify a target nucleic acid (e.g., cleave, methylate, demethylate, etc.) and/or a polypeptide associated with target nucleic acid (e.g., methylation, acetylation, etc., of, for example, a histone tail).

A Cas9 fusion polypeptide is a variant Cas9 polypeptide by virtue of differing in sequence from a wild type Cas9 polypeptide (e.g., a naturally occurring Cas9 polypeptide). A Cas9 fusion polypeptide is a Cas9 polypeptide (e.g., a wild type Cas9 polypeptide, a variant Cas9 polypeptide, a variant Cas9 polypeptide with reduced nuclease activity (as described above), and the like) fused to a covalently linked heterologous polypeptide (also referred to as a "fusion partner"). In some embodiments, a Cas9 fusion polypeptide is a variant Cas9 polypeptide with reduced nuclease activity (e.g., dCas9) fused to a covalently linked heterologous polypeptide. In some embodiments, the heterologous polypeptide exhibits (and therefore provides for) an activity (e.g., an enzymatic activity) that will also be exhibited by the Cas9 fusion polypeptide (e.g., methyltransferase activity, acetyltransferase activity, kinase activity, ubiquitinating activity, etc.). In some such embodiments, a method of binding, e.g., where the Cas9 polypeptide is a variant Cas9 polypeptide having a fusion partner (i.e., having a heterologous polypeptide) with an activity (e.g., an enzymatic activity) that modifies the target nucleic acid, the method can also be considered to be a method of modifying the target nucleic acid. In some embodiments, a method of binding a target nucleic acid (e.g., a single stranded target nucleic acid) can result in modification of the target nucleic acid. Thus, in some embodiments, a method of binding a target nucleic acid (e.g., a single stranded target nucleic acid) can be a method of modifying the target nucleic acid.

In some embodiments, the heterologous sequence provides for subcellular localization, i.e., the heterologous sequence is a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an endoplasmic reticulum (ER) retention signal, and the like). In some embodiments, a variant Cas9 does not include a NLS so that the protein is not targeted to the nucleus (which can be advantageous, e.g., when the target nucleic acid is an RNA that is present in the cytosol). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some embodiments, the heterologous sequence can provide for increased or decreased stability (i.e., the heterologous sequence is a stability control peptide, e.g., a degron, which in some embodiments is controllable (e.g., a temperature sensitive or drug controllable degron sequence, see below). In some embodiments, the heterologous sequence can provide for increased or decreased transcription from the target nucleic acid (i.e., the heterologous sequence is a transcription modulation sequence, e.g., a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (i.e., the heterologous sequence is a protein binding sequence, e.g., to provide the ability of a Cas9 fusion polypeptide to bind to another protein of interest, e.g., a DNA or histone modifying protein, a transcription factor or transcription repressor, a recruiting protein, an RNA modifaction enzyme, an RNA-binding protein, a translation initiation factor, an RNA splicing factor, etc.). A heterologous nucleic acid sequence may be linked to another nucleic acid sequence (e.g., by genetic engineering) to generate a chimeric nucleotide sequence encoding a chimeric polypeptide.

A subject Cas9 fusion polypeptide (Cas9 fusion protein) can have multiple (1 or more, 2 or more, 3 or more, etc.) fusion partners in any combination of the above. As an illustrative example, a Cas9 fusion protein can have a heterologous sequence that provides an activity (e.g., for transcription modulation, target modification, modification of a protein associated with a target nucleic acid, etc.) and can also have a subcellular localization sequence. In some embodiments, such a Cas9 fusion protein might also have a tag for ease of tracking and/or purification (e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). As another illustrative example, a Cas9 protein can have one or more NLSs (e.g., two or more, three or more, four or more, five or more, 1, 2, 3, 4, or 5 NLSs). In some embodiments, a fusion partner (or multiple fusion partners) (e.g., an NLS, a tag, a fusion partner providing an activity, etc.) is located at or near the C-terminus of Cas9. In some embodiments, a fusion partner (or multiple fusion partners) (e.g., an NLS, a tag, a fusion partner providing an activity, etc.) is located at the N-terminus of Cas9. In some embodiments, a Cas9 has a fusion partner (or multiple fusion partners) (e.g., an NLS, a tag, a fusion partner providing an activity, etc.) at both the N-terminus and C-terminus.

Suitable fusion partners that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled in part by the degron sequence. In some embodiments, a suitable degron is constitutive such that the degron exerts its influence on protein stability independent of experimental control (i.e., the degron is not drug inducible, temperature inducible, etc.) In some embodiments, the degron provides the variant Cas9 polypeptide with controllable stability such that the variant Cas9 polypeptide can be turned "on" (i.e., stable) or "off" (i.e., unstable, degraded) depending on the desired conditions. For example, if the degron is a temperature sensitive degron, the variant Cas9 polypeptide may be functional (i.e., "on", stable) below a threshold temperature (e.g., 42° C., 41° C., 40° C., 39° C., 38° C., 37° C., 36° C., 35° C., 34° C., 33° C., 32° C., 31° C., 30° C., etc.) but non-functional (i.e., "off", degraded) above the threshold temperature. As another example, if the degron is a drug inducible degron, the presence or absence of drug can switch the protein from an "off" (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g., Dohmen et al., Science, 1994. 263(5151): p. 1273-1276: Heat-inducible degron: a method for constructing temperature-sensitive mutants; Schoeber et al., Am J Physiol Renal Physiol. 2009 January;

296(1):F204-11: Conditional fast expression and function of multimeric TRPV5 channels using Shield-1; Chu et al., Bioorg Med Chem Lett. 2008 Nov. 15; 18(22):5941-4: Recent progress with FKBP-derived destabilizing domains; Kanemaki, Pflugers Arch. 2012 Dec. 28: Frontiers of protein expression control with conditional degrons; Yang et al., Mol Cell. 2012 Nov. 30; 48(4):487-8: Titivated for destruction: the methyl degron; Barbour et al., Biosci Rep. 2013 Jan. 18; 33(1): Characterization of the bipartite degron that regulates ubiquitin-independent degradation of thymidylate synthase; and Greussing et al., J Vis Exp. 2012 Nov. 10; (69): Monitoring of ubiquitin-proteasome activity in living cells using a Degron (dgn)-destabilized green fluorescent protein (GFP)-based reporter protein; all of which are hereby incorporated in their entirety by reference).

Exemplary degron sequences have been well-characterized and tested in both cells and animals. Thus, fusing Cas9 (e.g., wild type Cas9; variant Cas9; variant Cas9 with reduced nuclease activity, e.g., dCas9; and the like) to a degron sequence produces a "tunable" and "inducible" Cas9 polypeptide. Any of the fusion partners described herein can be used in any desirable combination. As one non-limiting example to illustrate this point, a Cas9 fusion protein (i.e., a chimeric Cas9 polypeptide) can comprise a YFP sequence for detection, a degron sequence for stability, and transcription activator sequence to increase transcription of the target nucleic acid. A suitable reporter protein for use as a fusion partner for a Cas9 polypeptide (e.g., wild type Cas9, variant Cas9, variant Cas9 with reduced nuclease function, etc.), includes, but is not limited to, the following exemplary proteins (or functional fragment thereof): his3, β-galactosidase, a fluorescent protein (e.g., GFP, RFP, YFP, cherry, tomato, etc., and various derivatives thereof), luciferase, β-glucuronidase, and alkaline phosphatase. Furthermore, the number of fusion partners that can be used in a Cas9 fusion protein is unlimited. In some embodiments, a Cas9 fusion protein comprises one or more (e.g. two or more, three or more, four or more, or five or more) heterologous sequences.

Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity, any of which can be directed at modifying nucleic acid directly (e.g., methylation of DNA or RNA) or at modifying a nucleic acid-associated polypeptide (e.g., a histone, a DNA binding protein, and RNA binding protein, and the like). Further suitable fusion partners include, but are not limited to boundary elements (e.g., CTCF), proteins and fragments thereof that provide periphery recruitment (e.g., Lamin A, Lamin B, etc.), and protein docking elements (e.g., FKBP/FRB, Pil1/Aby1, etc.).

Examples of various additional suitable fusion partners (or fragments thereof) for a subject variant Cas9 polypeptide include, but are not limited to those described in the PCT patent applications: WO2010/075303, WO2012/068627, and WO2013/155555 which are hereby incorporated by reference in their entirety.

Suitable fusion partners include, but are not limited to, a polypeptide that provides an activity that indirectly increases transcription by acting directly on the target nucleic acid or on a polypeptide (e.g., a histone, a DNA-binding protein, an RNA-binding protein, an RNA editing protein, etc.) associated with the target nucleic acid. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

Additional suitable fusion partners include, but are not limited to, a polypeptide that directly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.).

Non-limiting examples of fusion partners to accomplish increased or decreased transcription include transcription activator and transcription repressor domains (e.g., the Krüppel associated box (KRAB or SKD); the Mad mSIN3 interaction domain (SID); the ERF repressor domain (ERD), etc.). In some such embodiments, a Cas9 fusion protein is targeted by the guide nucleic acid to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some embodiments, the changes are transient (e.g., transcription repression or activation). In some embodiments, the changes are inheritable (e.g., when epigenetic modifications are made to the target nucleic acid or to proteins associated with the target nucleic acid, e.g., nucleosomal histones).

Non-limiting examples of fusion partners for use when targeting ssRNA target nucleic acids are include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); heliembodiments; RNA-binding proteins; and the like. It is understood that a fusion partner can include the entire protein or in some embodiments can include a fragment of the protein (e.g., a functional domain).

In some embodiments, the heterologous sequence can be fused to the C-terminus of the Cas9 polypeptide. In some embodiments, the heterologous sequence can be fused to the N-terminus of the Cas9 polypeptide. In some embodiments, the heterologous sequence can be fused to an internal portion (i.e., a portion other than the N- or C-terminus) of the Cas9 polypeptide.

In addition the fusion partner of a chimeric Cas9 polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3);

proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable fusion partner is a PUF RNA-binding domain, which is described in more detail in WO2012068627.

Some RNA splicing factors that can be used (in whole or as fragments thereof) as fusion partners for a Cas9 polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cis-elements that are located in either the core exon region or the exon extension region (i.e., between the two alternative 5' splice sites). For more examples, see WO2010075303.

In some embodiments, a Cas9 polypeptide (e.g., a wild type Cas9, a variant Cas9, a variant Cas9 with reduced nuclease activity, etc.) can be linked to a fusion partner via a peptide spacer.

In some embodiments, a Cas9 polypeptide comprises a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD attached to another molecule facilitates entry of the molecule into the nucleus (e.g., in some embodiments, a PTD includes a nuclear localization signal (NLS)). In some embodiments, a Cas9 polypeptide comprises two or more NLSs, e.g., two or more NLSs in tandem. In some embodiments, a PTD is covalently linked to the amino terminus of a Cas9 polypeptide. In some embodiments, a PTD is covalently linked to the carboxyl terminus of a Cas9 polypeptide. In some embodiments, a PTD is covalently linked to the amino terminus and to the carboxyl terminus of a Cas9 polypeptide. In some embodiments, a PTD is covalently linked to a nucleic acid (e.g., a guide nucleic acid, a polynucleotide encoding a guide nucleic acid, a polynucleotide encoding a Cas9 polypeptide, etc.). Exemplary PTDs include but are not limited to a minimal undecapeptide protein transduction domain (corresponding to residues 47-57 of HIV-1 TAT comprising YGRKKRRQRRR (SEQ ID NO: 38); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO: 39); Transportan GWTLNSAGYLLGKINLKALAALAKKIL (SEQ ID NO:40); KALAWEAKLAKALAKHLAKALAKALKCEA (SEQ ID NO:41); \ RQIKIWFQNRRMKWKK (SEQ ID NO: 42); RKKRRQRRR (SEQ ID NO: 43); RKKRRQRR (SEQ ID NO: 44); an arginine homopolymer of from 3 arginine residues to 50 arginine residues; YARAAARQARA (SEQ ID NO: 45); THRLPRRRRRR (SEQ ID NO: 46); and GGRRARRRRRR (SEQ ID NO: 47). In some embodiments, the PTD is an activatable CPP (ACPP) (Aguilera et al. (2009) *Integr Biol (Camb) June;* 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Donor Nucleic Acid

The composition can further comprise a donor nucleic acid. As used herein a "donor polynucleotide" is a nucleic acid that is inserted at the cleavage site induced by the RNA-guided endonuclease. The nucleic acid of the donor polynucleotide can be any type of nucleic acid known in the art. For example, the nucleic acid can be DNA, RNA, DNA/RNA hybrids, artificial nucleic acid or any combination thereof. In one embodiment, the nucleic acid of the donor polynucleotide is DNA, also known herein as "donor DNA."

In some embodiments, the donor nucleic acid is linked to the guide RNA, or to the crRNA or tracrRNA. For instance, the extension sequence can include a region that is sufficiently complementary to the donor nucleic acid to allow the donor nucleic acid to hybridize to the extension sequence of the guide RNA.

Alternatively, the donor nucleic acid can be covalently linked to the end of the extension sequence. Any suitable linkage can be used, many of which are known in the art. For instance, donor polynucleotide (e.g., donor DNA) covalently linked to the RNA-guided endonuclease via a self-immolative linker, or via click chemistry. By way of further illustration, the donor polynucleotide can be modified to include an appropriate functional group that facilitates conjugation, for instance, an azide, tetrazine, alkyne, strained alkene, or strained alkyne as appropriate to facilitate cycloaddition with an azide, tetrazine, alkyne, strained alkene, or strained alkyne on the linker molecule. The functional group can be attached to the donor nucleic acid by way of an optional spacer group. Techniques for modifying nucleic acids in this manner are known in the art, and such modified nucleic acids are commercially available. Once conjugated to the linker in this manner, the donor polynucleotide is attached to the RNA-guided endonuclease via a linkage comprising a triazole or cyclic alkene group. Other bioorthogonal chemistries can be used (e.g., thiol-ene) resulting the corresponding bioorthogonal linkage.

The donor polynucleotide is typically single-stranded, and serves as a template for the creation of double stranded DNA containing a desired sequence. The donor polynucleotide will contain sufficient identity (e.g., 85%, 90%, 95%, or 100% sequence identity) to a genomic sequence flanking the cleavage site to a region of the genomic sequence near the cleavage site (e.g., within about 50 bases or less, within about 30 bases or less, within about 15 bases or less, or within about 10 bases or less, within about 5 bases or less, or immediately adjacent the cleavage site) to support homology directed repair between the donor sequence and the genomic sequences flanking the cleavage site to which the donor sequence bears sufficient sequence identity. Donor polynucleotide sequences can be of any length, but must have a sufficient number of nucleotides bearing sequence identity on both sides of the cleavage site to facilitate HDR. These regions of the donor polynucleotide are known as homology arms. The homology arms can have the same number of bases or a different number of bases, and each are generally be at least 5 nucleotides in length (e.g., 10 nucleotides or more, 15 nucleotides or more, 20 nucleotides or more, 50 nucleotides or more, 100 nucleotides or more, 150 nucleotides or more, or even 200 nucleotides or more). The donor polynucleotide also contains a central region containing the mutation or other DNA sequence of interest, which is flanked by the homology arms. Thus, the overall length of the donor polynucleotide is typically greater than the total length of both homology arms (e.g., about 15 nucleotides or more, about 20 nucleotides or more, 50 nucleotides or more, 100 nucleotides or more, 150 nucleotides or more, or even 200 nucleotides or more 250 nucleotides or more, 500 nucleotides or more, 1000 nucleotides or more, 5000 nucleotides or more).

The donor polynucleotide sequence is typically not identical to the target genomic sequence. Rather, the donor polynucleotide sequence may contain one or more single base changes, insertions, deletions, inversion or rearrangements with respect to the genomic sequence, so long as the homology arms have sufficient sequence identity to support HDR. The donor polynucleotide sequence may further comprise sequences that facilitate detection of successful insertion of the donor polynucleotide.

The ends of the donor polynucleotide may be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

Cationic Polymers and Liposomal Systems

The composition comprises a vehicle or carrier, which can be any vehicle or carrier of the type used to deliver nucleic acids to cells. In one embodiment, the vehicle comprises a component that complexes with and/or encapsulates the modified guide RNA and, optionally, any other components of the CRISPR system included in the composition. For instance, the composition can comprise a cationic polymer or a cationic lipid.

Cationic polymers suitable for encapsulating a complex of the present invention include polycation-containing polymers that provide for enhanced escape from an endosomal compartment in a eukaryotic cell. Such polymers are referred to herein as "endosomal disruptive polymers." Any cationic polymer can be used. Examples of cationic endosomal disruptive polymers include polyethylene imine, poly (arginine), poly(lysine), poly(histidine), poly-[2-{(2-aminoethyl)amino}-ethyl-aspartamide] (pAsp(DET)), a block co-polymer of poly(ethylene glycol) (PEG) and poly(arginine), a block co-polymer of PEG and poly(lysine), and a block co-polymer of PEG and poly{N-[N-(2-aminoethyl)-2-aminoethyl]aspartamide} (PEG-pAsp(DET)), or a combination thereof. In some embodiments, a complex of the present disclosure comprises poly {N-[N-(2-aminoethyl)-2-aminoethyl]aspartamide} (PEG-pAsp(DET)). The CRISPR complex can be encapsulated in a single polymer layer, or multiple layers of the polymer.

In some embodiments, a complex of the present disclosure further includes a silicate in the portion of the complex that encapsulates the guide RNA and other elements of the CRISPR complex. For instance, the CRISPR complex can be encapsulated in alternating layers of an endosomal disruptive polymer and a silicate.

Cationic liposomes suitable for encapsulating a complex of the present invention include ({2,2-bis[(9Z,12Z)-Octadeca-9,12-dien-1-yl]-1,3-dioxan-5-yl}methyl) dimethylamine; (3aR,5s,6aS)-N,N-dimethyl-2,2-di((9Z,12Z)-octadeca-9,12-dien-1-yl)tetrahydro-3aH-cyclopenta[d][1,3]dioxol-5-amine; (3aR,5r,6aS)-N,N-dimethyl-2,2-di((9Z,12Z)-octadeca-9,12-dien-1-yl)tetrahydro-3aH-cyclopenta[d][1,3]dioxol-5-amine; (3aR,5R,7aS)-N,N-dimethyl-2,2-di((9Z,12Z)-octadeca-9,12-dien-1-yl)hexahydrobenzo[d][1,3]dioxol-5-amine; (3aS,5R,7aR)-N,N-dimethyl-2,2-di((9Z,12Z)-octadeca-9,12-dien-1-yl)hexahydrobenzo[d][1,3]dioxol-5-amine; (2-{2,2-bis[(9Z,12Z)-Octadeca-9,12-dien-1-yl]-1,3-dioxan-4-yl}ethyl)dimethylamine; (3aR,6aS)-5-methyl-2-(((6Z,9Z)-octadeca-6,9-dien-1-yl)-2-((9Z,12Z)-octadeca-9,12-dien-1-yl)tetrahydro-3aH-[1,3]dioxolo[4,5]pyrrole; (3aS,7aR)-5-methyl-2,2-di((9Z,12Z)-octadeca-9,12-dien-1-yl)hexahydro-[1,3]dioxolo[4,5-c]pyridine; (3aR,8aS)-6-methyl-2,2-di((9Z,12Z)-octadeca-9,12-dien-1-yl)hexahydro-3aH-[1,3]dioxolo[4,5-d]azepine; (6Z,9Z,28Z,31Z)-heptatriaconta-,9,28,31-tetraen-19-yl 2-(dimethylamino)acetate; (6Z,9Z,28Z,31Z)-heptatriaconta-6,9,28,31-tetraen-19-yl 3-(dimethylamino)propanoate; [6Z,9Z,28Z,31Z)-heptatriaconta-6,9,28,31-tetraen-19-yl-4-(dimethylamino)butanoate]; (6Z,9Z,28Z,31Z)-heptatriaconta-6,9,28,31-tetraen-19-yl5-(dimethylamino)pentanoate; (6Z,9Z,28Z,31Z)-heptatriaconta-6,9,28,31-tetraen-19-yl 6-(dimethylamino)hexanoate; (3-{2,2-bis[(9Z,12Z)-Octadeca-9,12-dien-1-yl]-1,3-dioxan-4-yl}propyl)dimethylamine; 1-((3aR,5r,6aS)-2,2-di((9Z,12Z)-octadeca-9,12-dien-1-yl)tetrahydro-3aHcyclopenta[d][1,3]dioxol-5-yl)-N,N-dimethylmethanamine; 1-((3aR,5s,6aS)-2,2-di((9Z,12Z)-octadeca-9,12-dien-1-yl)tetrahydro-3aHcyclopenta[d][1,3]dioxol-5-yl)-N,N-dimethylmethanamine; 8-methyl-2,2-di((9Z,12Z)-octadeca-9,12-dien-1-yl)-1,3-dioxa-8-azaspiro[4.5]decane; 2-(2,2-di((9Z,12Z)-octadeca-9,12-dien-1-yl)-1,3-dioxolan-4-yl)-N-methyl-N-(pyridin-3-ylmethyl)ethanamine; 1,3-bis(9Z,12Z)-Octadeca-9,12-dien-1-yl 2-[2-(dimethylamino)ethyl]propanedioate; N,N-dimethyl-1-((3aR,5R,7aS)-2-((8Z,11Z)-octadeca-8,11-dien-1-yl)-2-((9Z,12Z)-octadeca-9,12-dien-1-yl)hexahydrobenzo[d][1,3]dioxol-5-yl)methanamine; N,N-dimethyl-1-((3aR,5S,7aS)-2-((8Z,11Z)-octadeca-8,11-dien-1-yl)-2-((9Z,12Z)-octadeca-9,12-dien-1-yl)hexahydrobenzo[d][1,3]dioxol-5-yl)methanamine; (1s,3R,4S)-N,N-dimethyl-3,4-bis((9Z,12Z)-octadeca-9,12-dien-1-yloxy)cyclopentan amine; (1s,3R,4S)-N,N-dimethyl-3,4-bis((9Z,12Z)-octadeca-9,12-dien-1-yloxy)cyclopentan amine; 2-(4,5-di((8Z,11Z)-heptadeca-8,11-dien-1-yl)-2-methyl-1,3-dioxolan-2-yl)-N,N-dimethylethanamine; 2,3-di((8Z,11Z)-heptadeca-8,11-dien-1-yl)-N,N-dimethyl-1,4-dioxaspiro[4.5]decan-8-amine; (6Z,9Z,28Z,31Z)-heptatriaconta-6,9,28,31-tetraen-19-yl 4-(diethylamino)butanoate; (6Z,9Z,28Z,31Z)-heptatriaconta-6,9,28,31-tetraen-19-yl 4-[bis(propan-2-yl)amino]butanoate; N-(4-N,N-dimethylamino)butanoyl-(6Z,9Z,28Z,31Z)-heptatriaconta-6,9,28,31-tetraen-19-amine; (2-{2,2-bis[(9Z,12Z)-Octadeca-9,12-dien-1-yl]-1,3-dioxan-5-yl}ethyl)dimethylamine; (4-{2,2-bis[(9Z,12Z)-Octadeca-9,12-dien-1-yl]-1,3-dioxan-5-yl}butyl)dimethylamine; (6Z,9Z,28Z,31Z)-heptatriaconta-6,9,28,31-tetraen-19-yl (2-(dimethylamino)ethyl)carbamate; 2-(dimethylamino)ethyl (6Z,9Z,28Z,31Z)-heptatriaconta-6,9,28,31-tetraen-19-ylcarbamate; (6Z,9Z,28Z,31Z)-heptatriaconta-6,9,28,31-tetraen-19-yl3-(ethylamino)propanoate; (6Z,9Z,28Z,31Z)-heptatriaconta-6,9,28,31-tetraen-19-yl 4-(propan-2-ylamino)butanoate; N1,N1,N2-trimethyl-N2-((11Z,14Z)-2-((9Z,12Z)-octadeca-9,12-dien-1-yl)icosa-11,14-dien-1-yl)ethane-1,2-diamine; 3-(dimethylamino)-N-((11Z,14Z)-2-((9Z,12Z)-octadeca-9,12-dien-1-yl)icosa-11,14-dien-1-yl) propanamide; (6Z,9Z,28Z,31Z)-heptatriaconta-6,9,28,31-tetraen-19-yl 4-(methylamino)butanoate; Dimethyl({4-[(9Z,12Z)-octadeca-9,12-dien-1-yloxy]-3-{[(9Z,12Z)-octadeca-9,12-dien-1-yloxy]methyl}butyl})amine; 2,3-di((8Z,11Z)-heptadeca-8,11-dien-1-yl)-8-methyl-1,4-dioxa-8-azaspiro[4.5]decane; 3-(dimethylamino)propyl (6Z,9Z,28Z,31Z)-heptatriaconta-6,9,28,31-tetraen-19-ylcarbamate; 2-(dimethylamino)ethyl ((11Z,14Z)-2-((9Z,12Z)-octadeca-9,12-dien-1-yl)icosa-11,14-dien-1-yl)carbamate; 1-((3aR,4R,6aR)-6-methoxy-2,2-di((9Z,12Z)-octadeca-9,12-dien-1-yl)tetrahydrofuro[3,4-d][1,3]dioxol-4-yl)-N,N-imethylmethanamine; (6Z,9Z,28Z,31Z)-heptatriaconta-6,9,28,31-tetraen-19-yl 4-[ethyl(methyl)amino]butanoate; 6Z,9Z,28Z,31Z)-heptatriaconta-6,9,28,31-tetraen-19-yl 4-aminobutanoate; 3-(dimethylamino)propyl ((11Z,14Z)-2-((9Z,12Z)-octadeca-9,12-dien-1-yl)icosa-11,14-dien-1-yl) carbamate; 1-((3aR,4R,6aS)-2,2-di((9Z,12Z)-octadeca-9,12-dien-1-yl)tetrahydrofuro[3,4-d][1,3]dioxol-4-yl)-N,N-dimethylmethanamine; (3aR,5R,7aR)-N,N-dimethyl-2,2-di((9Z,12Z)-octadeca-9,12-dien-1-yl)hexahydrobenzo[d][1,3]dioxol-5-amine; (11Z,14Z)-N,N-dimethyl-2-((9Z,12Z)-octadeca-9,12-dien-1-yl)icosa-11,14-dien-1-amine; (3aS,4S,5R,7R,7aR)-N,N-dimethyl-2-((7Z,10Z)-octadeca-7,10-dien-1-yl)-2-((9Z,12Z)-octadeca-9,12-dien-1-yl)hexahydro-4,7-methanobenzo[d][1,3]dioxol-5-amine; N,N-dimethyl-3,4-bis((9Z,12Z)-octadeca-9,12-dien-1-yloxy)butan-1-amine; 3-(4,5-di((8Z,11Z)-heptadeca-8,11-dien-1-yl)-1,3-dioxolan-2-yl)-N,N-dimethylpropan-1-amine.

Nanoparticles

The composition comprising the guide RNA and, optionally, other components of the CRISPR system can further comprise a nanoparticle to which the guide RNA and, optionally, other components of CRISPR system are bound. For instance, the guide RNA, donor polynucleotide, or both, can be conjugated (linked or bound) to a nanoparticle. The nanoparticle, guide RNA and, optionally, other components of the CRISPR system can, in some embodiments, be further encapsulated in a cationic polymer and/or silicate as previously described. An example of a nanoparticle construct of this type is as described in International Patent Application No. PCT/US2016/052690.

Nanoparticles suitable for use in a complex of the present disclosure can be any shape and can range in size from about 5 nm to about 1000 nm in size, e.g., from about 5 nm to about 75 nm, about 5 to about 50 nm, about 5 nm to about 40 nm, about 10 nm to about 30, including about 20 nm to about 30 nm in size. Nanoparticles (e.g., gold nanoparticles) suitable for use in a complex of the present disclosure can have a size in the range from about 5 nm to about 150 nm, from about 100 nm to about 500 nm, from about 500 nm to 10 μm, or from about 10 μm to about 100 μm.

A nanoparticle can comprise any suitable material, preferably a biocompatible material. The biocompatible material can be a polymer. Suitable nanoparticle polymers include polystyrene, silicone rubber, polycarbonate, polyurethanes, polypropylenes, polymethylmethacrylate, polyvinyl chloride, polyesters, polyethers, and polyethylene. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D,L-lactide-co-PEO-co-D,L-lactide), poly(D, L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), and trimethylene carbonate, polyvinylpyrrolidone.

In some embodiments, the nanoparticle is a lipid nanoparticle. A lipid nanoparticle can include one or more lipids, and one or more of the polymers listed above.

In some embodiments, the nanoparticle is a metal nanoparticle, such as a colloidal metal particle. A colloidal metal includes any water-insoluble metal particle or metallic compound dispersed in liquid water. A colloid metal can be a suspension of metal particles in aqueous solution. The metal nanoparticle can be of any metal, including gold, silver, copper, nickel, aluminum, zinc, calcium, platinum, palladium, and iron. In some embodiments, gold nanoparticles are used. In some embodiments, the nanoparticles are non-gold nanoparticles that are coated with gold to make gold-coated nanoparticles.

Methods for making colloidal metal nanoparticles, including gold colloidal nanoparticles from $HAuCl_4$, are known to those having ordinary skill in the art. For example, the methods described herein as well as those described elsewhere (e.g., US 2001/005581; 2003/0118657; and 2003/0053983) can be used to make nanoparticles.

The guide RNA and, optionally, a donor polynucleotide, can be conjugated directly or indirectly to a nanoparticle surface. For example, a nucleic acid can be conjugated directly to the surface of a nanoparticle or indirectly through an intervening linker. Any type of molecule can be used as a linker. For example, a linker can be an aliphatic chain including at least two carbon atoms (e.g., 3, 4, 5, 6, 7, 8, 9, 10 or more carbon atoms), and can be substituted with one or more functional groups including ketone, ether, ester, amide, alcohol, amine, urea, thiourea, sulfoxide, sulfone, sulfonamide, and disulfide functionalities. In embodiments where the nanoparticle includes gold, a linker can be any thiol-containing molecule. Reaction of a thiol group with the gold results in a covalent sulfide (—S—) bond. Linker design and synthesis are well known in the art.

In some embodiments, the nucleic acid conjugated to the nanoparticle is a linker nucleic acid that serves to non-covalently bind one or more elements of the CRISPR system (e.g., guide RNA and/or donor nucleic acid) to the nanoparticle-nucleic acid conjugate. For instance, the linker nucleic acid can have a sequence that hybridizes to the guide nucleic acid or donor polynucleotide.

The nucleic acid conjugated to the nanoparticle (e.g., a colloidal metal (e.g., gold) nanoparticle; a nanoparticle comprising a biocompatible polymer) can have any suitable length. When the nucleic acid is a guide nucleic acid or donor polynucleotide, the length will be as suitable for such molecules, as discussed herein and known in the art. If the nucleic acid is a linker nucleic acid, it can have any suitable length for a linker, for instance, a length of from 10 nucleotides (nt) to 1000 nt, e.g., from about 1 nt to about 25 nt, from about 25 nt to about 50 nt, from about 50 nt to about 100 nt, from about 100 nt to about 250 nt, from about 250 nt to about 500 nt, or from about 500 nt to about 1000 nt. In some instances, the nucleic acid conjugated to the nanoparticle (e.g., a colloidal metal (e.g., gold) nanoparticle; a nanoparticle comprising a biocompatible polymer) nanoparticle can have a length of greater than 1000 nt.

When the nucleic acid linked (e.g., covalently linked; non-covalently linked) to a nanoparticle comprises a nucleotide sequence that hybridizes to at least a portion of the guide nucleic acid or donor polynucleotide present in a complex of the present disclosure, it has a region with sequence identity to a region of the complement of the guide nucleic acid or donor polynucleotide sequence sufficient to facilitate hybridization. In some embodiments, a nucleic acid linked to a nanoparticle in a complex of the present disclosure has at least 50%, at least 60%, at least 70%, at least 80%, at least 90%, at least 95%, at least 98%, at least 99%, or 100%, nucleotide sequence identity to a complement of from 10 to 50 nucleotides (e.g., from 10 nucleotides (nt) to 15 nt, from 15 nt to 20 nt, from 20 nt to 25 nt, from 25 nt to 30 nt, from 30 nt to 40 nt, or from 40 nt to 50 nt) of a guide nucleic acid or donor polynucleotide present in the complex.

Method of Genetically Modifying a Cell

The invention also provides a method of genetically modifying a target cell, particularly a eukaryotic target cell, using the modified guide RNA as described herein. The method comprises contacting the eukaryotic target cell with the modified guide RNA described herein, along with an RNA guided endonuclease or nucleic acid encoding same and, optionally, a donor nucleic acid. Upon entry into the cell, the modified guide RNA, RNA guided endonuclease, and optional donor nucleic acid edit a target site on a gene in the cell. The modified guide RNA, RNA guided endonuclease or nucleic acid encoding same, and optional donor nucleic acid may be in a composition as described herein.

In some embodiments, multiple guide RNAs (e.g., sgRNAs) can be delivered, each with a different targeting sequence, to effect editing at multiple sites. Such a method can be performed, for instance, using an sgRNA multimer as provided herein. Thus, also provided, is a method of editing two or more target sequences simultaneously, the method comprising contacting a cell comprising the two or more target sequences with a multimer as described herein, optionally with a donor nucleic acid, wherein the cell comprises an RNA-guided endonuclease or an RNA-guided endonuclease or nucleic acid encoding same is introduced into the cell, and wherein each sgRNA of the multimer comprises a different targeting sequence.

As used herein, a "target nucleic acid" or "target gene" is a polynucleotide (e.g., RNA, DNA) that is to be edited by the RNA guided endonuclease. A target nucleic acid or gene comprises a "target site" or "target sequence," which is a sequence present in a target nucleic to which the guide RNA hybridizes and, in turn, guides the endonuclease to the target site.

A "eukaryotic target cell" may be any eukaryotic cell known in the art and comprises both cells in vivo and in vitro. In an embodiment, the target cell is a mammalian cell.

The modified guide RNA, RNA-guided endonuclease, and optional donor DNA, or composition comprising same, can be administered via any suitable method, such as by direct contact of the composition with the cell.

The following examples further illustrate the invention but, of course, should not be construed as in any way limiting its scope.

Example 1

This example demonstrates the efficacy of a guide RNA modified with a structured extension.

Cas9 sgRNA were prepared with the same 20-nucleotide 5'-sequence targeting GPF. A non-extended sgRNA was used as a control. For the 3' extended sgRNA, the length of the extension was fixed at 35 nucleotides to examine the effect of different 35 nt sequences that fold into stable structures under physiological condition on knock-out efficiency. The tested extension sequences included random coils (R1, R2, and R3), a pseudoknot (S1), a quadraplex (S2), and stable hairpins (S3 and S4) (Table 1).

Figure 2:
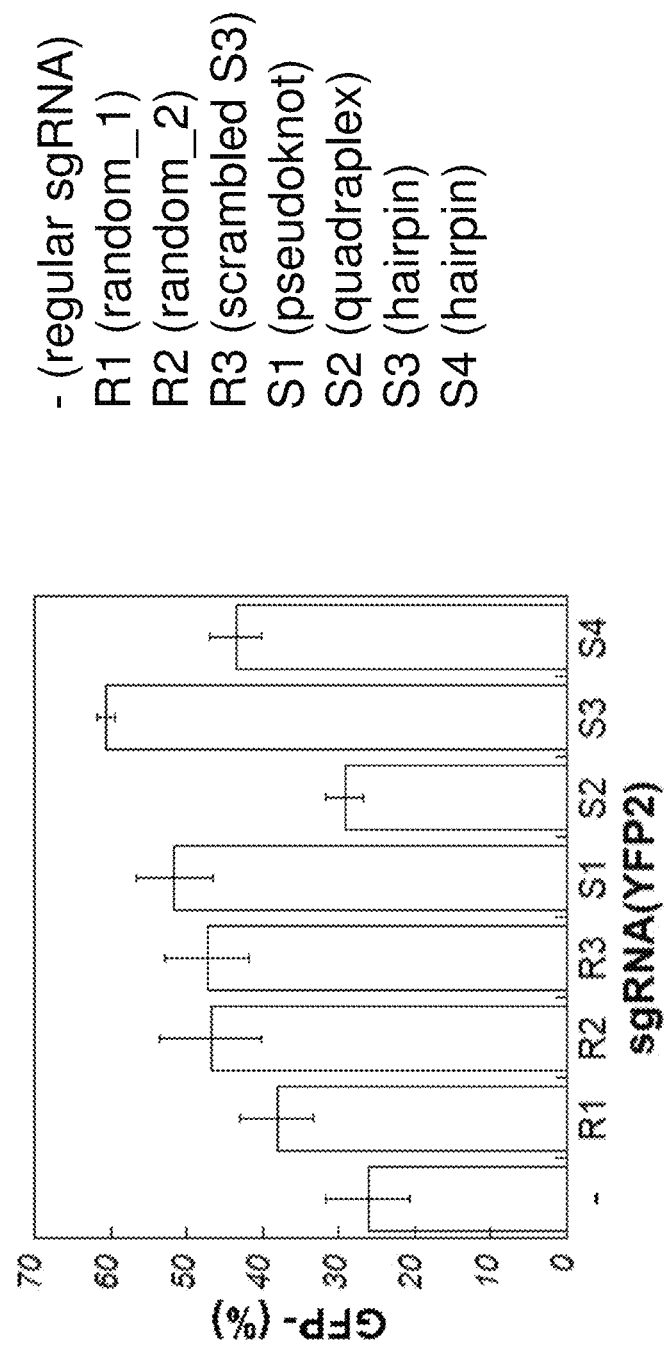
FIG. 2 is a graph of GFP knockout for various sgRNA in GFP-HEK cells.

The extended gRNA was transfected into HEK cells with LIPOFECTAMINE® (16 hours in OPTI-MEM® media (Gibco)) expressing green fluorescent protein (GFP-HEK cells), along with Cas9. Knockout efficiency was assessed based on a decrease in GFP fluorescence. The results are presented in FIG. 2.

The results show that all extended sgRNA outperformed the non-extended control sgRNA. The stable hairpin structure (S3) provided the best results in this experiment. S3-extended sgRNA was compared to non-extended sgRNA in GFP-HEK cells cultured in compete medium (10% serum), and the S3 extended RNA again demonstrated significantly higher knockout efficiency (data not shown).

Figure 3:
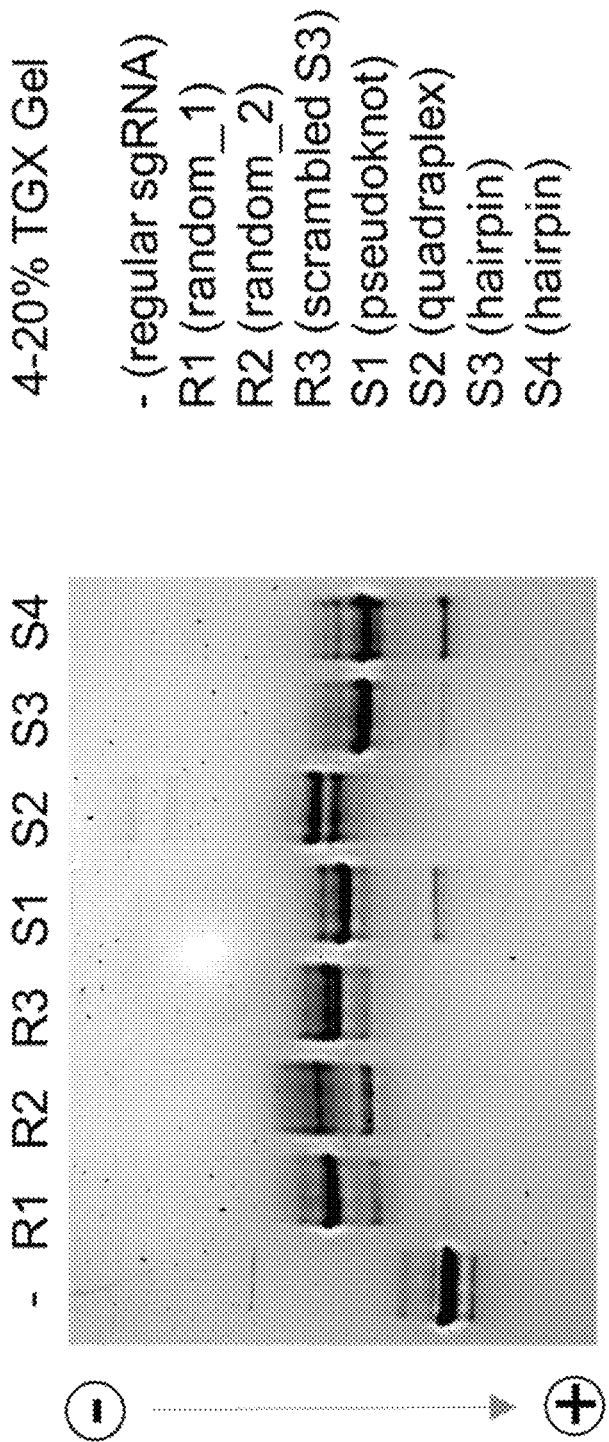
FIG. 3 is a gel electrophoretic separation of sgRNAs.

The sgRNAs were run on 7.5% TBE-PAGE (FIG. 3). The sgRNAs with 3'-extension (lane 2-8) have higher molecular weights, so they migrate more slowly than the non-extended sgRNA (lane 1). Among the sgRNA with a 3'-extension, S3 (lane 7) has the fastest mobility, and structures S1 (lane 5) and S4 (lane 8) had faster mobility than random coil R1. S1, S3, and S4 also had the highest knockout efficiency in GFP-HEK cells (although the improvement of S3 and S4 over the random coil was not statistically significant); thus, it is possible knockout efficiency correlates with the mobility or folded size of the extension.

TABLE 1

Representative RNA extended sequences (35 nucleotides) and their corresponding structures.

Sequences (5'→6')

| | |
|---|---|
| Random coil | R1 (SEQ ID NO: 31): UCCCGAGCUGUGCUUCGUUUCUACACUUGUACAUG<br>R2 (SEQ ID NO: 32): CCCUGCGACAGUCAUCUCGGCCGCCAAAGACACAG<br>R3 (SEQ ID NO: 33): UUCGUCGCCUUGGGCCGUCGUUUUCGCUCGUGGG |
| Pseudoknot | S1 (SEQ ID NO: 34): UUGGCGCAGUGGGCUAGCGCCACUCAAAAGGCCCA |

TABLE 1-continued

Representative RNA extended sequences (35 nucleotides) and their corresponding structures.

Sequences (5'→6')

| | |
|---|---|
| Quadraplex | S2 (SEQ ID NO: 35): UUAGGAGGAGGAGGAGGAGGAGGAGGAGGAGGAGG |
| Hairpin | S3 (SEQ ID NO: 36): UUCGUCGUCGUCGUCGUCGUCGUCGUCGUCGUCGU<br>S4 (SEQ ID NO: 37): UUCUGCUGCUGCUGCUGCUGCUGCUGCUGCUGCUG |

Example 2

Figure 4:
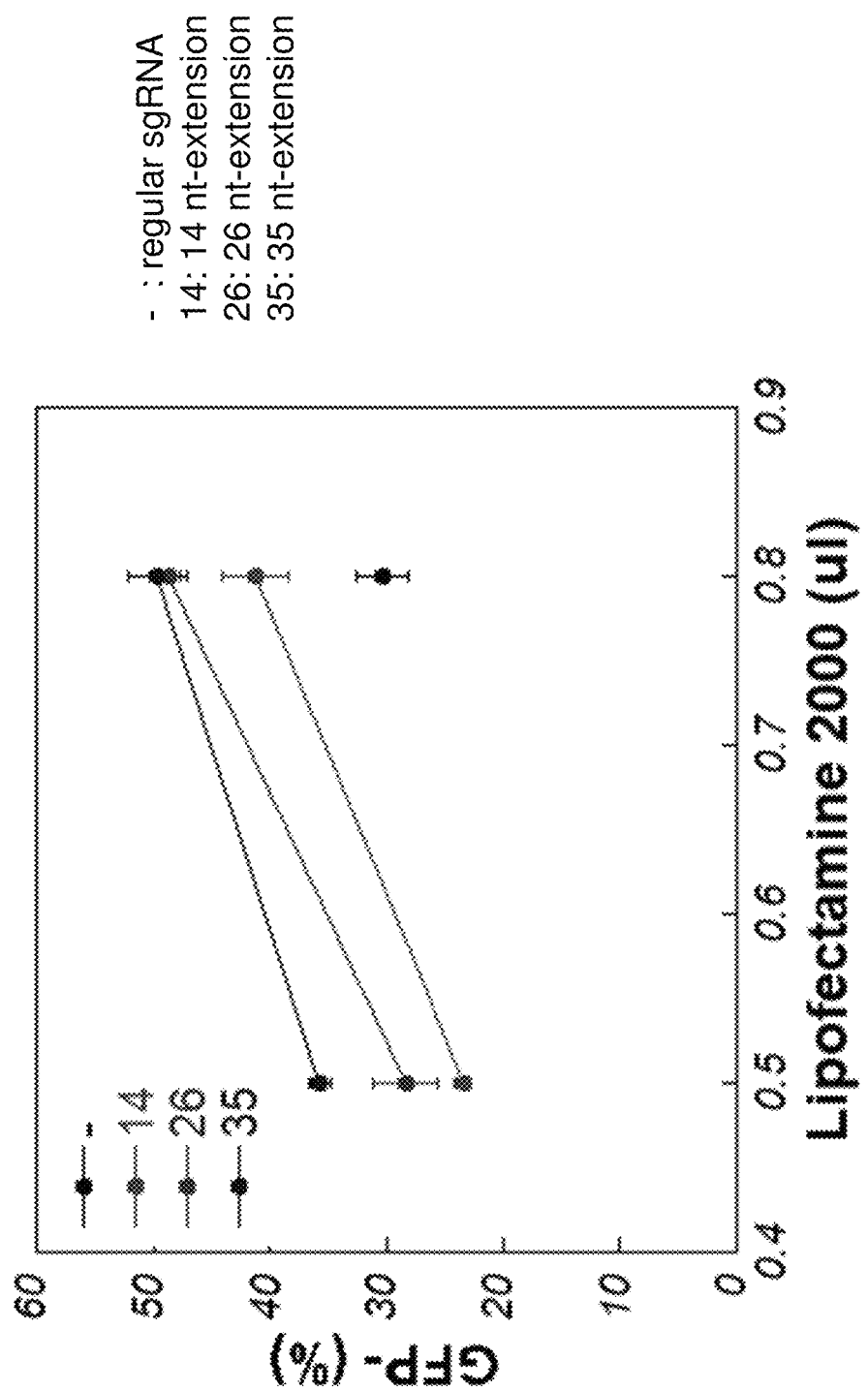
FIG. 4 is a graph of GFP knockout for sgRNA of different lengths in GFP-HEK cells plotted against the amount of transfection reagent used.

This example demonstrates the improved knockout efficiency produced using sgRNA with structured extensions.

sgRNA was prepared as in Example 1, but with stable hairpin structures of three different lengths: 14 nt, 26 nt, and 35 nt. Non-extended sgRNA was used as a control. The sgRNA were tested for knockout efficiency by transfection into GFP-HEK cells using LIPOFECTAMINE® (Invitrogen) with Cas9. The results are provided in FIG. 4.

The sgRNA extended with stable hairpins of all tested lengths enhanced knockout efficiency as compared to the non-extended sgRNA, with the longer extensions tending to provide better knockout efficiency than the shorter extensions in this test.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A modified sgRNA or tracrRNA comprising an extension sequence on the 3' end of the sgRNA or tracrRNA, wherein the extension sequence comprises about 8 nucleotides or more, wherein the extension sequence comprises a repeating trinucleotide motif, and wherein the repeating trinucleotide motif comprises CAA, UUG, AAG, CUU, CCU, CCA, UAA, or a combination thereof;

CAU, CUA, UUA, AUG, UAG, or a combination thereof;

CGA, CGU, CGG, CAG, CUG, CCG, or a combination thereof;

a CNG motif, or combination of CNG motifs, optionally with CGA or CGU; or

AGG, UGG, or combination thereof.

2. The modified sgRNA or tracrRNA of claim 1, wherein the extension sequence comprises about 20 nucleotides or more.

3. The modified sgRNA or tracrRNA of claim 1, wherein the extension sequence is a random coil.

4. The modified sgRNA or tracrRNA of claim 1, wherein the extension sequence comprises a self-hybridizing sequence.

5. The modified sgRNA or tracrRNA of claim 1, wherein the extension sequence comprises a semi-stable hairpin structure, a stable hairpin structure, a pseudoknot structure, a G-quadraplex structure, a bulge loop structure, an internal loop structure, a branch loop structure, or a combination thereof.

6. The modified tracrRNA of claim 1, wherein the modified tracrRNA is hybridized to a crRNA to form a dgRNA.

7. The modified sgRNA or tracrRNA of claim 1, wherein the extension sequence has a structure that provides a negative charge density greater than a random coil nucleic acid sequence with the same number of nucleic acids.

8. The modified sgRNA or tracrRNA of claim 1, wherein the extension sequence is not an aptamer sequence.

9. A composition comprising the modified sgRNA or tracrRNA of claim 1 and a vehicle.

10. The composition of claim 9, wherein the vehicle comprises a cationic polymer or cationic lipid, optionally with a neutral helper lipid.

11. The composition of claim 9, wherein the vehicle is complexed with the sgRNA or tracrRNA and, optionally, encapsulates the sgRNA or tracrRNA.

12. The composition of claim 9, wherein the composition further comprises an RNA-guided endonuclease or nucleic acid encoding same, and wherein the RNA-guided endonuclease is optionally a Cas9 polypeptide.

13. The composition of claim 9, wherein the composition further comprises a donor nucleic acid.

14. The composition of claim 13, wherein the donor nucleic acid is covalently linked to the modified sgRNA or tracrRNA or is hybridized to the modified sgRNA or tracrRNA, optionally to the extension sequence of the modified sgRNA.

15. A method of editing a gene in a cell, the method comprising contacting the cell with the modified sgRNA or tracrRNA of claim 1, or a composition comprising the modified sgRNA or tracerRNA of claim 1, optionally with a donor nucleic acid,
- wherein the cell comprises an RNA-guided endonuclease, or an RNA-guided endonuclease or nucleic acid encoding the RNA-guided endonuclease is introduced into the cell,
- whereupon the modified sgRNA or tracrRNA enters the cell and a target gene in the cell is edited.

16. The method of claim 15, wherein the modified sgRNA, or a dgRNA comprising the modified tracrRNA, comprises a targeting sequence that hybridizes to the target gene.

17. The method of claim 15, wherein the modified sgRNA or tracrRNA is administered as part of a composition further comprising an RNA guided endonuclease or nucleic acid encoding the RNA-guided endonuclease, and the RNA guided endonuclease is introduced into the cell by contacting the cell with the composition.

18. The method of claim 15, wherein the RNA-guided endonuclease is Cas9.

19. The method of claim 15, wherein the method comprises contacting the cell with the modified sgRNA or tracrRNA of claim 1, or a composition comprising the modified sgRNA or tracerRNA of claim 1, and a donor nucleic acid.

20. A multimer comprising two or more sgRNA molecules of claim 1, wherein the extension sequence of each sgRNA molecule is joined to the extension sequence of another sgRNA molecule by base pairing to form the multimer;
or
a multimer comprising two or more sgRNA molecules of claim 1 each of which comprises an extension sequence in the tetraloop or stem-loop 2 position of the sgRNA, wherein the extension sequence of each sgRNA molecule is joined to the extension sequence of another sgRNA molecule by base pairing to form the multimer.

21. A method of editing two or more target sequences simultaneously, the method comprising contacting a cell comprising the two or more target sequences with the multimer of claim 20, optionally with a donor nucleic acid,
- wherein the cell comprises an RNA-guided endonuclease or an RNA-guided endonuclease or nucleic acid encoding the RNA-guide endonuclease is introduced into the cell, and wherein each sgRNA of the multimer comprises a different targeting sequence;
- whereupon the modified sgRNA enters the cell and a target gene in the cell is edited.

22. The method of claim 21, wherein the method comprising contacting a cell comprising the two or more target sequences with the multimer of claim 20 and a donor nucleic acid.

* * * * *

SEQUENCE LISTING

```
<160> NUMBER OF SEQ ID NOS: 53

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Ser Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335
```

```
Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
            690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750
```

Arg His Lys Pro Glu Asn Ile Val Ile Glu Met Ala Arg Glu Asn Gln
              755                 760                 765

Thr Thr Gln Lys Gly Gln Lys Asn Ser Arg Gly Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser

-continued

```
                1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Ile Gly Leu Asp Ile Gly Thr Asn Ser Val Gly Trp Ala Val Ile
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Ile Gly Leu Asp Ile Gly Thr Asn Ser Val Gly Trp Ala Val Ile
1               5                   10                  15

<210> SEQ ID NO 4
<211> LENGTH: 27
<212> TYPE: PRT
<213> ORGANISM: Artificial Sequence
<220> FEATURE:
<223> OTHER INFORMATION: Synthetic

<400> SEQUENCE: 4

Asp Val Asp His Ile Val Pro Gln Ser Phe Leu Lys Asp Asp Ser Ile
1               5                   10                  15
```

Asp Asn Lys Val Leu Thr Arg Ser Asp Lys Asn
            20                  25

<210> SEQ ID NO 5
<211> LENGTH: 8
<212> TYPE: PRT
<213> ORGANISM: Artificial Sequence
<220> FEATURE:
<223> OTHER INFORMATION: Synthetic

<400> SEQUENCE: 5

His His Ala His Asp Ala Tyr Leu
1               5

<210> SEQ ID NO 6
<211> LENGTH: 76
<212> TYPE: RNA
<213> ORGANISM: Artificial Sequence
<220> FEATURE:
<223> OTHER INFORMATION: Synthetic

<400> SEQUENCE: 6
guuuuagagc uagaaauagc aaguuaaaau aaggcuaguc cguuaucaac uugaaaagu      60 ggcaccgagu cggugc                                                    76

<210> SEQ ID NO 7
<211> LENGTH: 86
<212> TYPE: RNA
<213> ORGANISM: Artificial Sequence
<220> FEATURE:
<223> OTHER INFORMATION: Synthetic

<400> SEQUENCE: 7
guuuaagagc uaugcuggaa acagcauagc aaguuuaaau aaggcuaguc cguuaucaac     60
uugaaaaagu ggcaccgagu cggugc                                         86

<210> SEQ ID NO 8
<211> LENGTH: 86
<212> TYPE: RNA
<213> ORGANISM: Artificial Sequence
<220> FEATURE:
<223> OTHER INFORMATION: Synthetic

<400> SEQUENCE: 8
guuucagagc uaugcuggaa acagcauagc aaguugaaau aaggcuaguc cguuaucaac     60
uugaaaaagu ggcaccgagu cggugc                                         86

<210> SEQ ID NO 9
<211> LENGTH: 86
<212> TYPE: RNA
<213> ORGANISM: Artificial Sequence
<220> FEATURE:
<223> OTHER INFORMATION: Synthetic

<400> SEQUENCE: 9
guuuaagagc uaugcuggaa acagcauagc aaguuuaaau aaggcuaguc cguuaucaac     60
uugaaaaagu ggcaccgagu cggugc                                         86

<210> SEQ ID NO 10
<211> LENGTH: 76
<212> TYPE: RNA
<213> ORGANISM: Artificial Sequence
<220> FEATURE:

<223> OTHER INFORMATION: Synthetic

<400> SEQUENCE: 10
guuuuagagc uagaaauagc aaguuaaaau aaggcuaguc cguuaucaac uugaaaaagu    60
ggcaccgagu cggugc    76

<210> SEQ ID NO 11
<211> LENGTH: 76
<212> TYPE: RNA
<213> ORGANISM: Artificial Sequence
<220> FEATURE:
<223> OTHER INFORMATION: Synthetic

<400> SEQUENCE: 11
guuuuagagc uagaaauagc aaguuaaaau aaggcuaguc cguuaucaac uugaaaaagu    60
ggcaccgagu cggugc    76

<210> SEQ ID NO 12
<211> LENGTH: 107
<212> TYPE: RNA
<213> ORGANISM: Artificial Sequence
<220> FEATURE:
<223> OTHER INFORMATION: Synthetic

<400> SEQUENCE: 12
guuguagcuc ccuuucucga aaagagaacc guugcuacaa uaaggccguc ugaaaagaug    60
ugccgcaacg cucugccccu aaagcuucu gcuuuaggg gcuuuuu    107

<210> SEQ ID NO 13
<211> LENGTH: 121
<212> TYPE: RNA
<213> ORGANISM: Artificial Sequence
<220> FEATURE:
<223> OTHER INFORMATION: Synthetic

<400> SEQUENCE: 13
guuguagcuc ccuuucucau uucggaaacg aaaugagaac cguugcuaca auaaggccgu    60
cugaaaagau gugccgcaac gcucugcccc uuaaagcuuc ugcuuuaggg ggcaucguuu    120
a    121

<210> SEQ ID NO 14
<211> LENGTH: 121
<212> TYPE: RNA
<213> ORGANISM: Artificial Sequence
<220> FEATURE:
<223> OTHER INFORMATION: Synthetic

<400> SEQUENCE: 14
guuguagcuc ccuuucucau uucggaaacg aaaugagaac cguugcuaca auaaggccgu    60
cugaaaagau gugccgcaac gcucugcccc uuaaagcuuc ugcuuuaggg ggcaucguuu    120
a    121

<210> SEQ ID NO 15
<211> LENGTH: 93
<212> TYPE: RNA
<213> ORGANISM: Artificial Sequence
<220> FEATURE:
<223> OTHER INFORMATION: Synthetic

<400> SEQUENCE: 15
guuuuuguac ucucaagauu caauaaucuu gcagaagcua caaagauaag gcuucaugcc    60
gaaaucaaca cccgucauu uuauggcagg gug                             93

<210> SEQ ID NO 16
<211> LENGTH: 93
<212> TYPE: RNA
<213> ORGANISM: Artificial Sequence
<220> FEATURE:
<223> OTHER INFORMATION: Synthetic

<400> SEQUENCE: 16 guuuuguac ucucaagauu caauaaucuu gcagaagcua caaagauaag gcuucaugcc   60
gaaaucaaca cccgucauu uuauggcagg gug                             93

<210> SEQ ID NO 17
<211> LENGTH: 87
<212> TYPE: RNA
<213> ORGANISM: Artificial Sequence
<220> FEATURE:
<223> OTHER INFORMATION: Synthetic

<400> SEQUENCE: 17 guuuuguac ucucagaaau gcagaagcua caaagauaag gcuucaugcc gaaaucaaca   60 cccgucauu uuauggcagg guguuuu                                    87

<210> SEQ ID NO 18
<211> LENGTH: 99
<212> TYPE: RNA
<213> ORGANISM: Artificial Sequence
<220> FEATURE:
<223> OTHER INFORMATION: Synthetic

<400> SEQUENCE: 18
gucuuuguac ucucaagauu uaagaaauua aaucuugcag aagcuacaaa gauaaggcuu   60
caugccgaaa ucaacacccu gucauucuau ggcagggug                      99

<210> SEQ ID NO 19
<211> LENGTH: 125
<212> TYPE: RNA
<213> ORGANISM: Artificial Sequence
<220> FEATURE:
<223> OTHER INFORMATION: Synthetic

<400> SEQUENCE: 19 guuuuguac ucucaagauu uaaguaacug uacaacgaaa cuuacacagu uacuuaaauc   60
uugcagaagc uacaaagaua aggcuucaug ccgaaaucaa cacccguca uuuauggca   120 gggug                                                          125

<210> SEQ ID NO 20
<211> LENGTH: 80
<212> TYPE: RNA
<213> ORGANISM: Artificial Sequence
<220> FEATURE:
<223> OTHER INFORMATION: Synthetic

<400> SEQUENCE: 20 guuuuguac ucugguacca gaagcuacaa agauaaggcu ucaugccgaa aucaacaccc   60
ugucauuuua uggcagggug                                          80

<210> SEQ ID NO 21
<211> LENGTH: 76
<212> TYPE: RNA

-continued

<213> ORGANISM: Artificial Sequence
<220> FEATURE:
<223> OTHER INFORMATION: Synthetic

<400> SEQUENCE: 21
guuuuuguac ucgaaagaag cuacaaagau aaggcuucau gccgaaauca acacccuguc    60
auuuuauggc agggug                                                   76

<210> SEQ ID NO 22
<211> LENGTH: 92
<212> TYPE: RNA
<213> ORGANISM: Artificial Sequence
<220> FEATURE:
<223> OTHER INFORMATION: Synthetic

<400> SEQUENCE: 22
guuuuagagc uguguuguuu guuaaaacaa cacagcgagu aaaauaagg cuuaguccgu     60 acucaacuug aaaagguggc accgauucgg ug                                  92

<210> SEQ ID NO 23
<211> LENGTH: 94
<212> TYPE: RNA
<213> ORGANISM: Artificial Sequence
<220> FEATURE:
<223> OTHER INFORMATION: Synthetic

<400> SEQUENCE: 23
guuuuagagc uguguuguuu cgguuaaaac aacacagcga guuaaaauaa ggcuuaguuc    60
guacucaacu ugaaaaggug gcaccgauuc ggug                                94

<210> SEQ ID NO 24
<211> LENGTH: 78
<212> TYPE: RNA
<213> ORGANISM: Artificial Sequence
<220> FEATURE:
<223> OTHER INFORMATION: Synthetic

<400> SEQUENCE: 24
guuuuagagc ugggua ccca gcgaguuaaa auaaggcuua guccguacuc aacuugaaaa    60
gguggcaccg auucggug                                                  78

<210> SEQ ID NO 25
<211> LENGTH: 76
<212> TYPE: RNA
<213> ORGANISM: Artificial Sequence
<220> FEATURE:
<223> OTHER INFORMATION: Synthetic

<400> SEQUENCE: 25
guuuuaguac ucuggaaaca gaaucuacua aaacaaggca aaaugccgug uuuaucucgu    60
caacuuguug gcgaga                                                   76

<210> SEQ ID NO 26
<211> LENGTH: 84
<212> TYPE: RNA
<213> ORGANISM: Artificial Sequence
<220> FEATURE:
<223> OTHER INFORMATION: synthetic

<400> SEQUENCE: 26
guuuuaguac ucuguaauga aaauuacaga aucuacuaaa acaaggcaaa augccguguu    60
uaucucguca acuuguuggc gaga                                          84

<210> SEQ ID NO 27
<211> LENGTH: 124
<212> TYPE: RNA
<213> ORGANISM: Artificial Sequence
<220> FEATURE:
<223> OTHER INFORMATION: Synthetic

<400> SEQUENCE: 27
guuuuaguac ucuguaauuu uagguaugag guagacgaaa auuguacuua uaccuaaaau    60
uacagaaucu acuaaaacaa ggcaaaaugc cguguuuauc ucgucaacuu guuggcgaga   120
uccg                                                               124

<210> SEQ ID NO 28
<211> LENGTH: 133
<212> TYPE: RNA
<213> ORGANISM: Artificial Sequence
<220> FEATURE:
<223> OTHER INFORMATION: Synthetic

<400> SEQUENCE: 28
guuugagagu uguguaauuu aagauggauc ucaaagaaau uuaagaucca ucuuaaauua    60
cacaacgagu ucaaauaaga auucaucaaa aucgucccuu uugggaccgc ucauugugga   120
gcaucuuuuu uuu                                                     133

<210> SEQ ID NO 29
<211> LENGTH: 133
<212> TYPE: RNA
<213> ORGANISM: Artificial Sequence
<220> FEATURE:
<223> OTHER INFORMATION: Synthetic

<400> SEQUENCE: 29
guuugagagu uguguaauuu aagauggauc ucaaagaaau uuaagaucca ucuuaaauua    60
cacaacgagu ucaaauaaga auucaucaaa aucgucccuu uugggaccgc ucauugugga   120
gcaucuuuuu uuu                                                     133

<210> SEQ ID NO 30
<211> LENGTH: 109
<212> TYPE: RNA
<213> ORGANISM: Artificial Sequence
<220> FEATURE:
<223> OTHER INFORMATION: Synthetic

<400> SEQUENCE: 30
guuugagagu uguguaauuu aaggaaacuu aaauuacaca acgaguucaa auaagaauuc    60
aucaaaaucg ucccuuuugg gaccgcucau uguggagcau cuuuuuuuu              109

<210> SEQ ID NO 31
<211> LENGTH: 35
<212> TYPE: RNA
<213> ORGANISM: Artificial Sequence
<220> FEATURE:
<223> OTHER INFORMATION: Synthetic

<400> SEQUENCE: 31
ucccgagcug ugcuucguuu cuacacuugu acaug                              35

<210> SEQ ID NO 32
<211> LENGTH: 35
<212> TYPE: RNA

```
<213> ORGANISM: Artificial Sequence
<220> FEATURE:
<223> OTHER INFORMATION: Synthetic

<400> SEQUENCE: 32
cccugcgaca gucaucucgg ccgccaaaga cacag                                35

<210> SEQ ID NO 33
<211> LENGTH: 35
<212> TYPE: RNA
<213> ORGANISM: Artificial Sequence
<220> FEATURE:
<223> OTHER INFORMATION: Synthetic

<400> SEQUENCE: 33
uucgucgccu ugggccgucg uuuuucgcuc guggg                                35

<210> SEQ ID NO 34
<211> LENGTH: 35
<212> TYPE: RNA
<213> ORGANISM: Artificial Sequence
<220> FEATURE:
<223> OTHER INFORMATION: Synthetic

<400> SEQUENCE: 34
uuggcgcagu gggcuagcgc cacucaaaag gccca                                35

<210> SEQ ID NO 35
<211> LENGTH: 35
<212> TYPE: RNA
<213> ORGANISM: Artificial Sequence
<220> FEATURE:
<223> OTHER INFORMATION: Synthetic

<400> SEQUENCE: 35
uuaggaggag gaggaggagg aggaggagga ggagg                                35

<210> SEQ ID NO 36
<211> LENGTH: 35
<212> TYPE: RNA
<213> ORGANISM: Artificial Sequence
<220> FEATURE:
<223> OTHER INFORMATION: Synthetic

<400> SEQUENCE: 36
uucgucgucg ucgucgucgu cgucgucguc gucgu                                35

<210> SEQ ID NO 37
<211> LENGTH: 35
<212> TYPE: RNA
<213> ORGANISM: Artificial Sequence
<220> FEATURE:
<223> OTHER INFORMATION: Synthetic

<400> SEQUENCE: 37
uucugcugcu gcugcugcug cugcugcugc ugcug                                35

<210> SEQ ID NO 38
<211> LENGTH: 11
<212> TYPE: PRT
<213> ORGANISM: Artificial Sequence
<220> FEATURE:
<223> OTHER INFORMATION: Synthetic

<400> SEQUENCE: 38

Tyr Gly Arg Lys Lys Arg Arg Gln Arg Arg Arg
```

<210> SEQ ID NO 39
<211> LENGTH: 12
<212> TYPE: PRT
<213> ORGANISM: Artificial Sequence
<220> FEATURE:
<223> OTHER INFORMATION: Synthetic

<400> SEQUENCE: 39

Arg Arg Gln Arg Arg Thr Ser Lys Leu Met Lys Arg
1               5                   10

<210> SEQ ID NO 40
<211> LENGTH: 27
<212> TYPE: PRT
<213> ORGANISM: Artificial Sequence
<220> FEATURE:
<223> OTHER INFORMATION: Synthetic

<400> SEQUENCE: 40

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 41
<211> LENGTH: 33
<212> TYPE: PRT
<213> ORGANISM: Artificial Sequence
<220> FEATURE:
<223> OTHER INFORMATION: Synthetic

<400> SEQUENCE: 41

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 42
<211> LENGTH: 16
<212> TYPE: PRT
<213> ORGANISM: Artificial Sequence
<220> FEATURE:
<223> OTHER INFORMATION: Synthetic

<400> SEQUENCE: 42

Arg Gln Ile Lys Ile Trp Phe Gln Asn Arg Arg Met Lys Trp Lys Lys
1               5                   10                  15

<210> SEQ ID NO 43
<211> LENGTH: 9
<212> TYPE: PRT
<213> ORGANISM: Artificial Sequence
<220> FEATURE:
<223> OTHER INFORMATION: Snthetic

<400> SEQUENCE: 43

Arg Lys Lys Arg Arg Gln Arg Arg Arg
1               5

<210> SEQ ID NO 44
<211> LENGTH: 8
<212> TYPE: PRT

```
<213> ORGANISM: Artificial Sequence
<220> FEATURE:
<223> OTHER INFORMATION: Synthetic

<400> SEQUENCE: 44

Arg Lys Lys Arg Arg Gln Arg Arg
1               5

<210> SEQ ID NO 45
<211> LENGTH: 11
<212> TYPE: PRT
<213> ORGANISM: Artificial Sequence
<220> FEATURE:
<223> OTHER INFORMATION: Synthetic

<400> SEQUENCE: 45

Tyr Ala Arg Ala Ala Ala Arg Gln Ala Arg Ala
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic

<400> SEQUENCE: 46

Thr His Arg Leu Pro Arg Arg Arg Arg Arg Arg
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Synthetic

<400> SEQUENCE: 47

Gly Gly Arg Arg Ala Arg Arg Arg Arg Arg Arg
1               5                   10

<210> SEQ ID NO 48
<211> LENGTH: 100
<212> TYPE: RNA
<213> ORGANISM: Artificial Sequence
<220> FEATURE:
<223> OTHER INFORMATION: Synthetic

<400> SEQUENCE: 48
ggggccacua gggacaggau guuuuagagc uagaaauagc aaguuaaaau aaggcuaguc     60
cguuaucaac uugaaaaagu ggcaccgagu cggugcuuuu                         100

<210> SEQ ID NO 49
<211> LENGTH: 48
<212> TYPE: DNA
<213> ORGANISM: Artificial Sequence
<220> FEATURE:
<223> OTHER INFORMATION: Synthetic

<400> SEQUENCE: 49
ggacatcgat gtcacctcca atgactaggg tggagacaac gatctcat                48

<210> SEQ ID NO 50
<211> LENGTH: 48
<212> TYPE: DNA
<213> ORGANISM: Artificial Sequence
```

```
<220> FEATURE:
<223> OTHER INFORMATION: Synthetic

<400> SEQUENCE: 50
atgagatcgt tgtctccacc ctagtcattg gaggtgacat cgatgtcc                48

<210> SEQ ID NO 51
<211> LENGTH: 42
<212> TYPE: RNA
<213> ORGANISM: Artificial Sequence
<220> FEATURE:
<223> OTHER INFORMATION: Synthetic

<400> SEQUENCE: 51
gucaccucca augacuaggg guuuuagagc uaugcuguuu ug                     42

<210> SEQ ID NO 52
<211> LENGTH: 82
<212> TYPE: RNA
<213> ORGANISM: Artificial Sequence
<220> FEATURE:
<223> OTHER INFORMATION: Synthetic

<400> SEQUENCE: 52
ggaaccauuc aaaacagcau agcaaguuaa aauaaggcua guccguuauc aacuugaaaa   60
agugcaccga gucggugcuu uu                                           82

<210> SEQ ID NO 53
<211> LENGTH: 99
<212> TYPE: RNA
<213> ORGANISM: Artificial Sequence
<220> FEATURE:
<223> OTHER INFORMATION: Synthetic

<400> SEQUENCE: 53
gucaccucca augacuaggg guuuuagagc uagaaauagc aaguuaaaau aaggcuaguc   60
cguuaucaac uugaaaaagu gcaccgaguc ggugcuuuu                         99
```